United States Patent
Keller et al.

(10) Patent No.: US 9,816,799 B2
(45) Date of Patent: Nov. 14, 2017

(54) EMBROIDERED STRAIN SENSING ELEMENTS

(71) Applicant: Oculus VR, LLC, Menlo Park, CA (US)

(72) Inventors: Sean Jason Keller, Kirkland, WA (US); Tristan Thomas Trutna, Seattle, WA (US); David R. Perek, Bellevue, WA (US); Bruce A. Cleary, III, Seattle, WA (US); Brian Michael Scally, Seattle, WA (US)

(73) Assignee: Oculus VR, LLC, Menlo Park, CA (US)

( * ) Notice: Subject to any disclaimer, the term of this patent is extended or adjusted under 35 U.S.C. 154(b) by 0 days.

(21) Appl. No.: 14/975,465

(22) Filed: Dec. 18, 2015

(65) Prior Publication Data
US 2017/0176167 A1    Jun. 22, 2017

(51) Int. Cl.
*G01B 7/16* (2006.01)
*G01L 1/22* (2006.01)
*A61F 9/02* (2006.01)
*A41D 19/00* (2006.01)

(52) U.S. Cl.
CPC ........... *G01B 7/18* (2013.01); *A41D 19/0006* (2013.01); *A61F 9/02* (2013.01); *G01L 1/225* (2013.01); *G01L 1/2287* (2013.01)

(58) Field of Classification Search
CPC ......... G01B 7/18; A41D 19/0006; A61F 9/02; G01L 1/225; G01L 1/2287
USPC .................................. 73/760, 768, 774, 775
See application file for complete search history.

(56) References Cited

U.S. PATENT DOCUMENTS

| | | | |
|---|---|---|---|
| 6,360,615 B1 * | 3/2002 | Smela ................. | A61B 5/1124 73/862.474 |
| 6,568,275 B2 | 5/2003 | Scholz et al. | |
| 7,255,011 B2 | 8/2007 | Morimoto | |
| 7,726,199 B2 | 6/2010 | Shkel et al. | |
| 7,750,790 B2 * | 7/2010 | Yang ........................ | G01L 1/22 338/114 |
| 8,032,199 B2 * | 10/2011 | Linti .................. | A41D 13/1281 600/388 |
| 8,079,269 B2 | 12/2011 | Chakraborty | |

(Continued)

FOREIGN PATENT DOCUMENTS

KR    10-2014-0022180 A    2/2014

OTHER PUBLICATIONS

PCT International Search Report and Written Opinion, PCT Application No. PCT/US2016/048734, dated Nov. 21, 2016, 23 pages.

*Primary Examiner* — Max Noori
(74) *Attorney, Agent, or Firm* — Fenwick & West LLP

(57) ABSTRACT

A deformation sensing fabric comprises a fabric substrate comprising a first fabric layer and a first conductive element woven into the first fabric layer. The first conductive element outputs a first instrumented signal, responsive to an applied stimulus signal, indicative of a measure of change in an electrical property of the first conductive element in response to a strain applied to the fabric substrate along a long-axis of the first conductive element. The first conductive element is instrumented by a measurement system which stimulates the first conductive element and measures an electrical property of the first conductive element.

14 Claims, 14 Drawing Sheets

(56) References Cited

U.S. PATENT DOCUMENTS

| | | |
|---|---|---|
| 8,191,433 B2 * | 6/2012 | Tao ..................... D06M 11/74 |
| | | 73/763 |
| 8,661,915 B2 | 3/2014 | Taylor |
| 9,119,916 B2 * | 9/2015 | Heppe ................ A61M 1/3653 |
| 2010/0002402 A1 | 1/2010 | Rogers et al. |
| 2010/0036287 A1 | 2/2010 | Weber |
| 2013/0134992 A1 | 5/2013 | Zhu et al. |
| 2014/0090488 A1 | 4/2014 | Taylor et al. |
| 2014/0204285 A1 | 7/2014 | Jang |
| 2014/0238153 A1 | 8/2014 | Wood et al. |
| 2015/0250420 A1 | 9/2015 | Longinotti-Buitoni |
| 2015/0373831 A1 | 12/2015 | Rogers et al. |
| 2016/0003880 A1 | 1/2016 | Deschildre et al. |
| 2017/0020413 A1 | 1/2017 | Otaka et al. |
| 2017/0089782 A1 | 3/2017 | Hirt et al. |

\* cited by examiner

Fabric Sensor 400

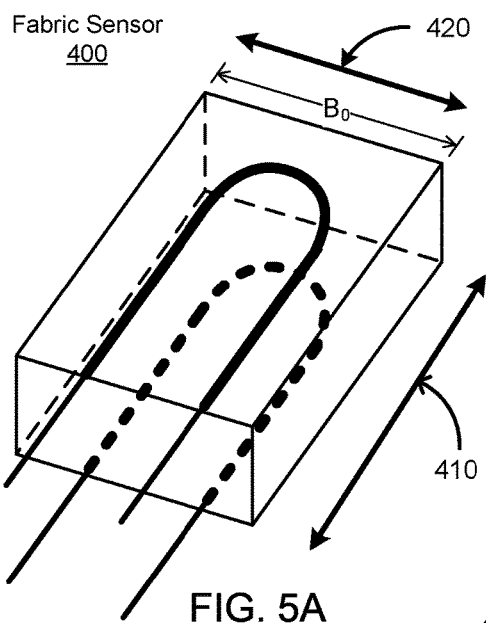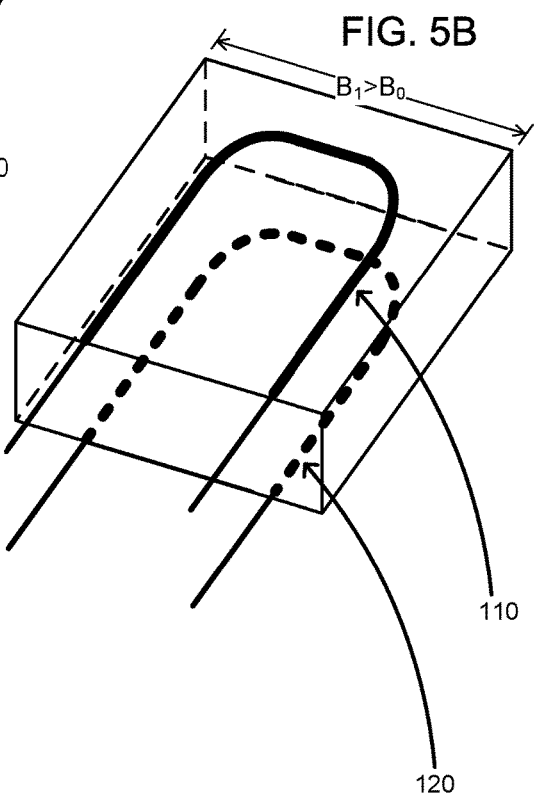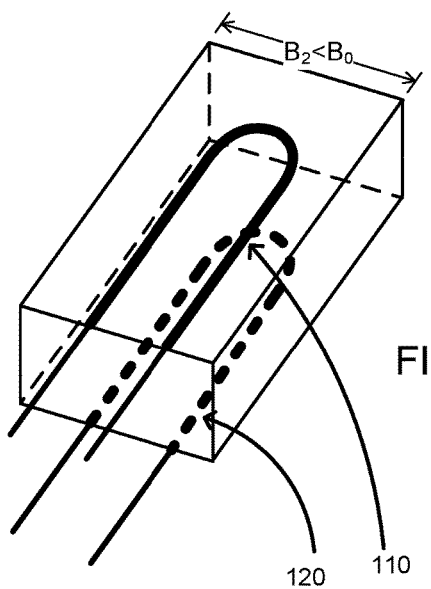
FIG. 5A
FIG. 5B
FIG. 5C

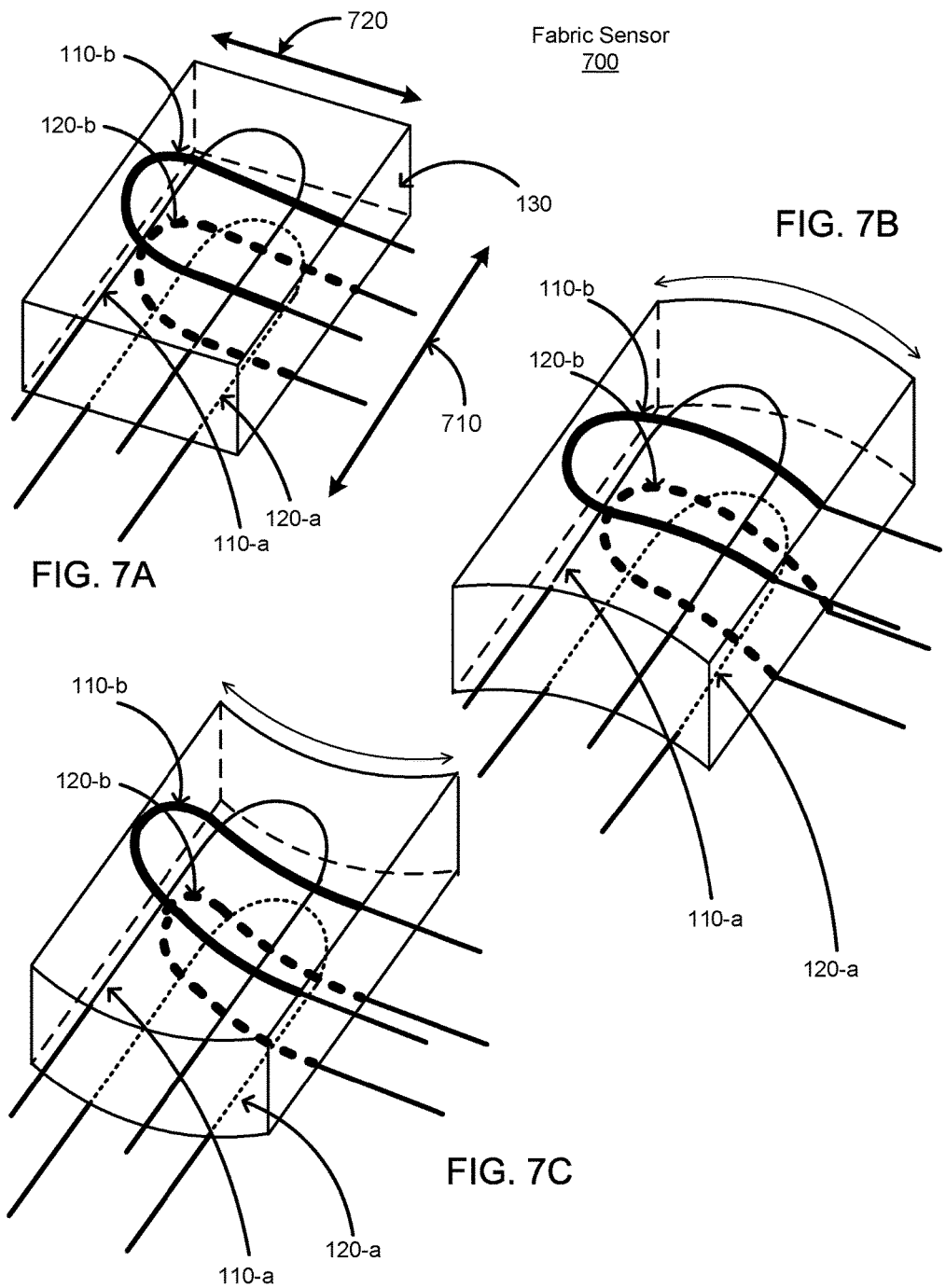

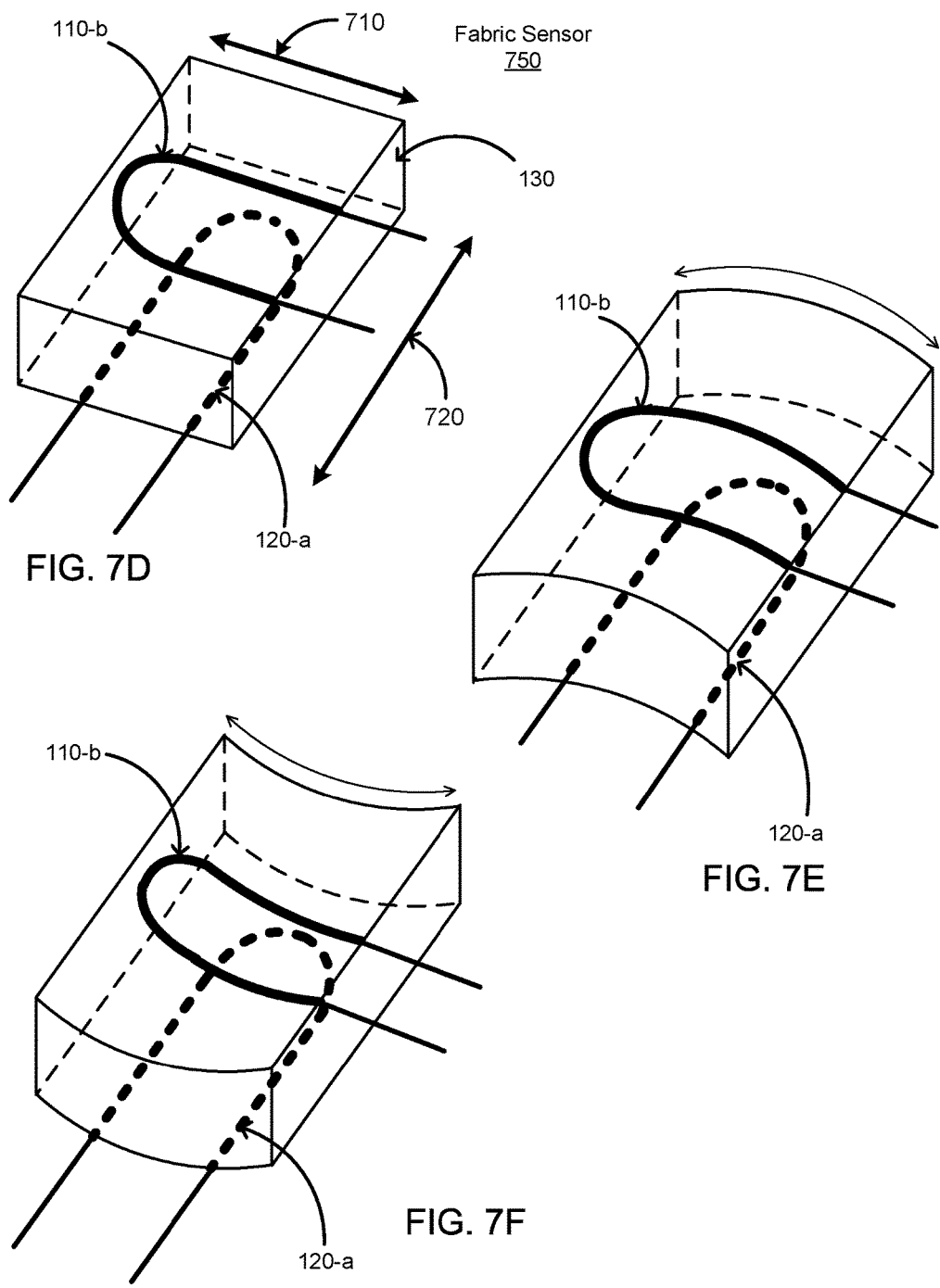

EMBROIDERED STRAIN SENSING ELEMENTS

BACKGROUND

Fabrics and textile materials are commonly used in wearable devices and soft goods. Such textiles frequently undergo large ranges of deformation, for instance, in the form of stretches and bends. These ranges of strains and bends are challenging to measure in soft textiles. Typical strain sensing elements such as metal foil strain gauges or carbon-based resistive bending sensors are limited in their ability to deform or stretch under applied strain, interfere with the feel and function of the textile, and inhibit the ability of the fabric to breathe naturally resulting in discomfort in wearable applications.

SUMMARY

According to some embodiments, deformation sensing fabric comprises a fabric substrate with a first fabric layer and a first conductive element woven into the first fabric layer. In some embodiments, the first conductive element is terminated to enable the first conductive element to be interfaced (e.g., connected) to a measuring instrument. The first conductive element is optionally made from electrically conductive elastic yarn or fabric material that is interwoven, embroidered, or otherwise intertwined into the first fabric layer. The first conductive element is configured to output a first signal indicative of a measure of change in an electrical property of the first conductive element in response to a strain applied to the fabric substrate along a long-axis of the first conductive element. For example, the first conductive element is interfaced to an instrument which provides a stimulus signal to the first conductive element and the instrument measures the first signal output from the first conductive element in response to the stimulus signal. The instrument measures an electrical property (e.g., resistance) of the first conductive element which changes in response to deformation along a given axis (e.g., the long axis) of the first conductive element; the instrument then determines a measure of deformation based on the measured electrical property.

In some embodiments, the first conductive element is configured to form a first strain gauge and the first signal (e.g., instrumented signal produced responsive to a stimulus input) is indicative of a change in resistance of the first strain gauge in response to a strain applied to the fabric substrate along an axis (e.g., sensing axis, such as a length) of the first strain gauge.

Additionally, in some embodiments, the fabric substrate is a multilayer fabric comprising a second fabric layer and an electrically insulating interstitial layer formed between the first and second fabric layers. In some embodiments, each layer of the multilayer fabric comprises one or more weaves, threads, or other fabric materials stacked along a plane perpendicular to a plane in which the first conductive element is formed. In such embodiments, the deformation sensing fabric further comprises a second conductive element interwoven into threads of the second fabric layer, the second conductive element configured to output a second signal (e.g., instrumented signal produced responsive to a stimulus input provided to the second conductive element) in response to a strain applied in the same first direction. For example, the second conductive element is configured to form a second strain gauge and the second signal (e.g., instrumented/measured signal produced responsive to a stimulus input provided to the second conductive element) is indicative of a change in resistance of the second strain gauge in response to a strain applied to the fabric substrate along a length of the second strain gauge.

Alternatively, a fabric is designed to have two interwoven conductive elements (a first and second conductive element) each of which exhibits limited electrical conductivity (at lower than a threshold value of signal frequencies, such as at DC or substantially 0 Hz) with respect to the other. The two conductive elements are woven into the fabric with a geometry designed to result in capacitive coupling to the other in a predefined manner over different deformations of the fabric, for example through interdigitated extensions of each element. In such embodiments, the first element comprises a first set of fingers (e.g., finger-like extensions) interwoven into the first fabric layer along the long axis of the first conductive element, the first set of fingers physically and electrically connected by and extending along a first direction from a first base embroidered into the first fabric layer. The second element comprises a second set of fingers alternating with the first set of fingers and interwoven along the long axis of the first conductive element, the second set of fingers physically and electrically connected by and extending along a second direction from a second base embroidered into the first fabric layer, the second direction opposite and parallel to the first direction. In such embodiments, the first set of fingers are physically separated from the second set of fingers. In such embodiments, the first signal represents an increase in capacitance between the interdigitated elements in response to a strain applied to the fabric substrate along lengths of the first and second sets of fingers. On the other hand, the first signal represents a decrease in capacitance between the interdigitated elements in response to a strain applied to the fabric substrate perpendicular to the lengths of the first and second sets of fingers.

BRIEF DESCRIPTION OF THE DRAWINGS

FIGS. 5A-5C illustrate breadth-wise stress deformations applied to a fabric strain sensor, according to one or more embodiments.

FIGS. 7A-7F illustrate breadth-wise flex deformations applied to a fabric strain sensor, according to one or more embodiments.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Figure 1A:
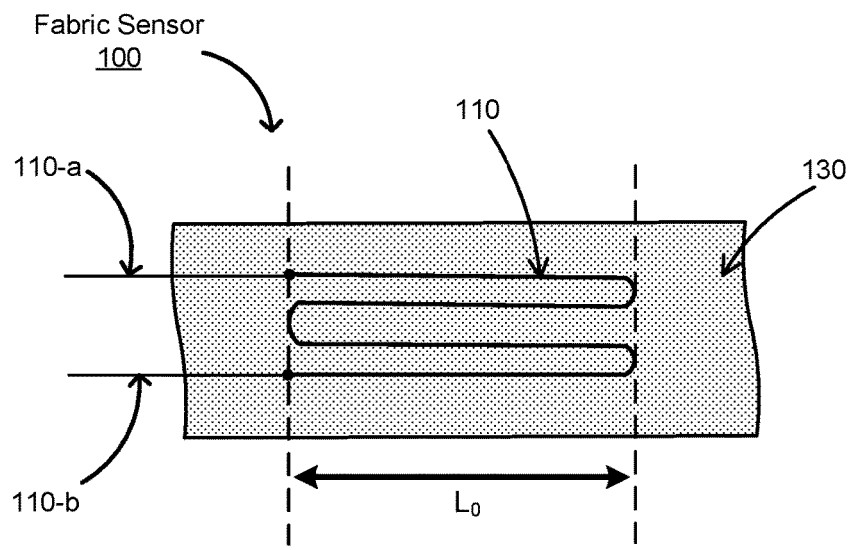
FIGS. 1A-1B illustrate views of a fabric strain sensor with a resistive strain gauge embroidered into a surface of the fabric, with (FIG. 1B) and without (FIG. 1A) applied strain, in accordance with one or more embodiments.
Figure 1B:
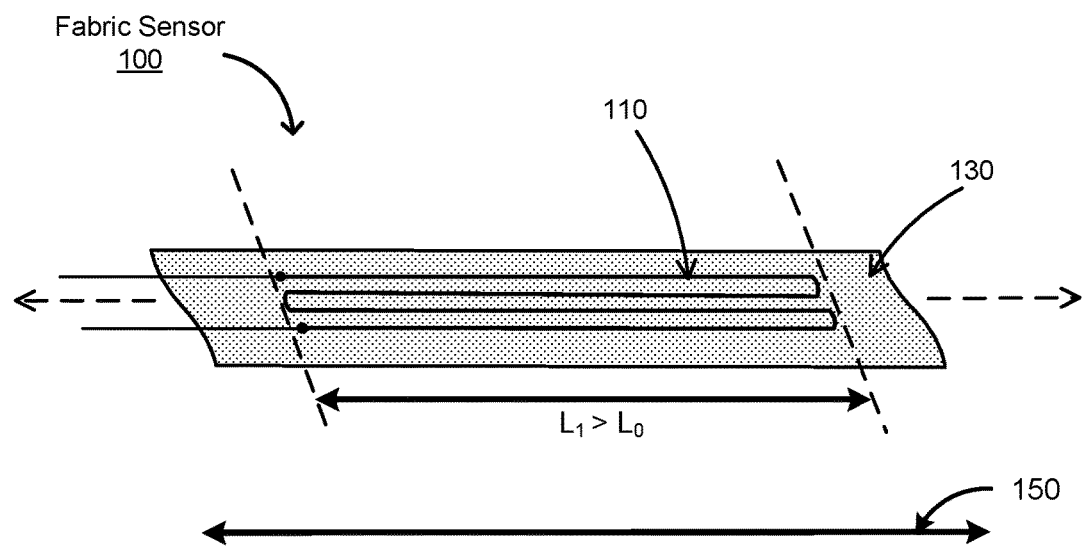

FIGS. 1A-1B illustrate views of a fabric strain sensor 100 with a strain gauge embroidered into a surface of a fabric substrate 130, in accordance with one or more embodiments.

In some embodiments, a specialized electrically conductive yarn is interwoven into a layer of fabric material, using embroidery or weaving techniques, to construct one or more strain sensing elements within the fabric for use in soft goods or wearable devices. In such embodiments, the interwoven pattern is designed such that deformation of the fabric substrate would change electrical properties of the conductive yarn.

FIGS. 1A-1B illustrate a fabric sensor 100 comprising an electrically conductive element (a strain gauge) 110 intertwined (or embroidered) into (or onto) a surface of the fabric substrate 130. A length of the strain gauge 110 increases (from $L_0$ to $L_1 > L_0$) as the fabric substrate is deformed along a long-axis (length dimension 150) of the strain gauge, as shown in FIGS. 1A-1B. This change in length (L) can be measured based on a change in resistance (R) of the strain gauge 110, given resistivity ($\rho$) and cross-sectional area (A), based on the formula.

$$\Delta L \cong \frac{A \Delta R}{\rho} \quad (1)$$

In other words, the deformation sensing fabric 100 comprises a fabric substrate 130 comprising a first fabric layer, and a first conductive element 110 woven into the first fabric layer. The first conductive element 110 is configured to output a first signal indicative of a measure of change in an electrical property (e.g., electrical resistance) of the first conductive element in response to a strain applied to the fabric substrate 130 along a long-axis (dimension 150) of the first conductive element.

In some embodiments, the first fabric layer comprises an electrically insulating fiber material and the first strain gauge comprises an electrically conductive elastic fiber material interwoven (e.g., sewn, embroidered, or otherwise intertwined) amidst threads of the electrically insulating fiber material. For example, the first conductive element is made from electrically conductive yarn, of an elastic textile fabric material, such as neoprene fibers.

In some embodiments, the electrically conductive elastic fiber material is encapsulated by an electrically insulating elastic fiber material coating configured to be interwoven amidst threads of the electrically insulating fiber material and configured to deform corresponding to deformation of the first strain gauge. For example, the electrically insulating encapsulation prevents electrical discharge, electrostatic run-off, or electrical shorting when current or charge flow through the first strain gauge element, since the strain gauge element, if formed on the surface of the fabric substrate, can come in contact with human body parts. For example, the conductive yarn is over-molded with silicone or an elastomer, or a yarn with other interwoven fibers such as neoprene.

As illustrated in FIG. 1A, the first strain gauge comprises a meandering pattern of electrically conductive elastic yarn interwoven in the first fabric layer, the meandering interwoven pattern comprises one or more arcuate heads and a plurality of parallel elongate leads extending from ends of the one or more arcuate heads, the parallel leads formed along the length of the first strain gauge. In such embodiments, the meandering interwoven pattern of electrically conductive elastic yarn forms a continuous electrically conductive path. The first strain-gauge 110 has two distinct terminals, a first terminal 110-a and a second terminal 110-b, formed at two ends of the continuous electrically conductive yarn; the first signal is measurable across the first and second terminals of the first strain-gauge.

FIGS. 2A-2D illustrate views of a fabric strain sensor 200 with an interdigitated fabric elements embroidered into a surface of the fabric substrate 130, in accordance with one or more embodiments, with (FIGS. 2B, 2D) and without (FIGS. 2A, 2C) applied strain, in accordance with one or more embodiments.

Figure 2A:
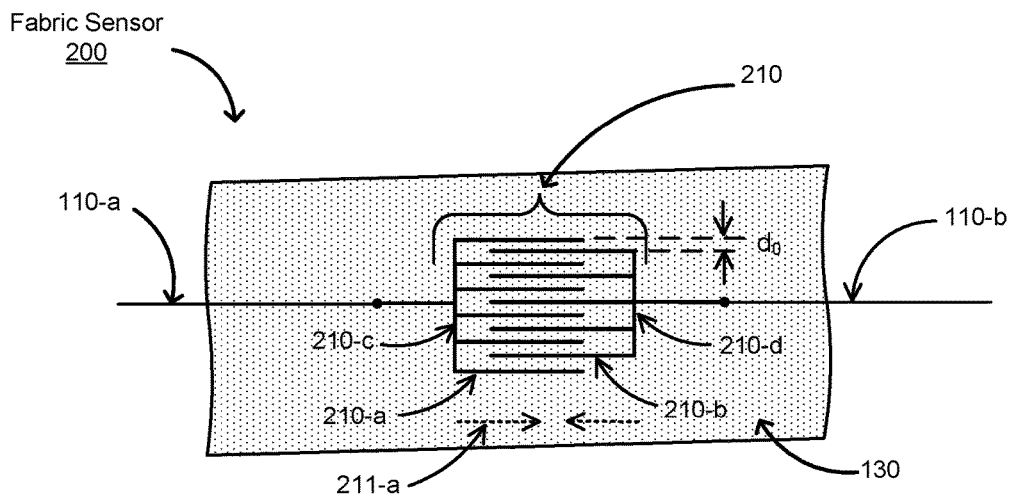
FIGS. 2A-2D illustrate views of a fabric strain sensor with an interdigitated fabric capacitor embroidered into a surface of a fabric substrate, with (FIGS. 2B, 2D) and without (FIGS. 2A, 2C) applied strain, in accordance with one or more embodiments.
Figure 2B:
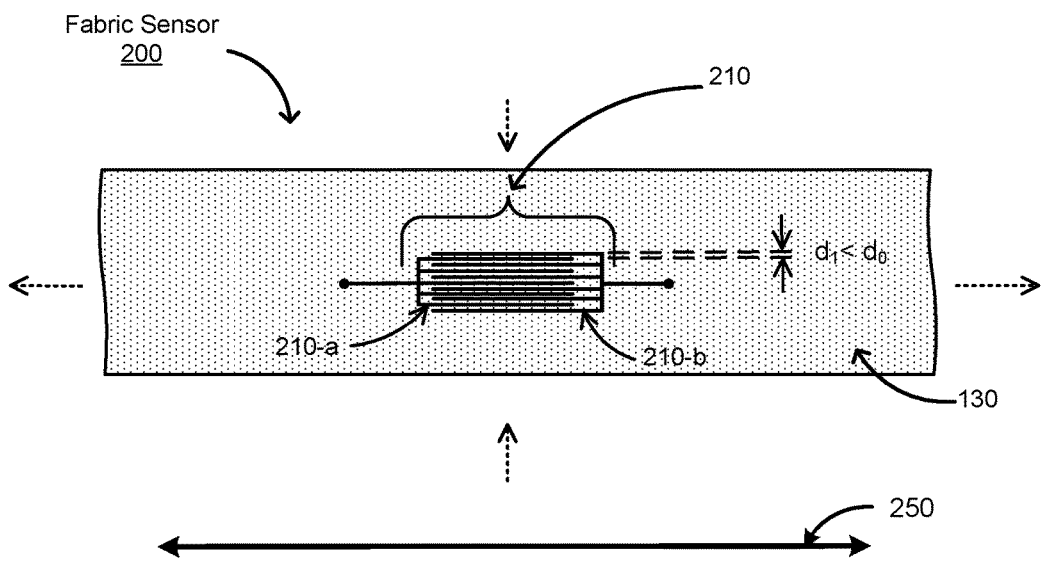
Figure 2C:
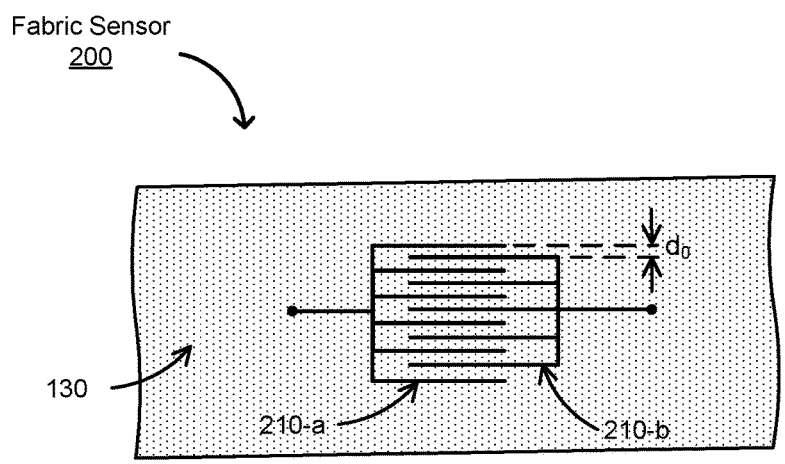
Figure 2D:
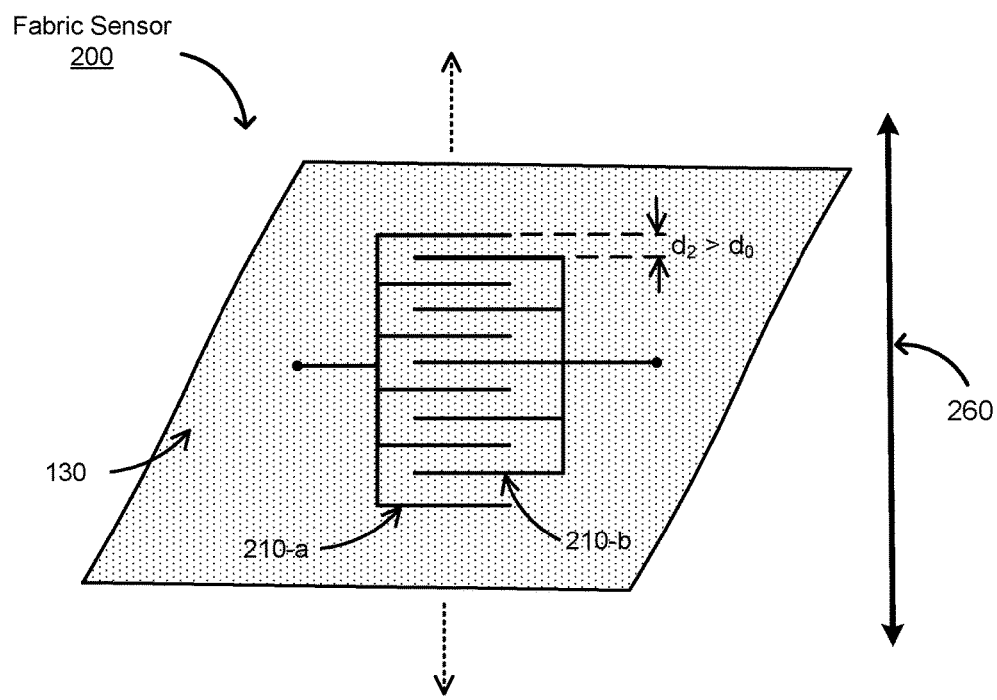

In some embodiments, and as illustrated in FIG. 2A, the first and second electrically conductive element (jointly illustrated as 210) comprise two combs or sets of fingers (210-a and 210-b) that are sewn or embroidered with a conductive material. The fingers of the two sets are interdigitated, but physically isolated, and are configured to be capacitively coupled in response to applied electrical stimulation. The electrical capacitance between the two sets of fingers 210-a and 210-b is inversely proportional to the space or distance (d) between adjacent fingers. As illustrated in FIGS. 2C-2D, if the fabric substrate 130 is stretched along a length of the fingers (dimension 250), the gap between adjacent fingers of the elements decreases (e.g., from $d_0$ to $d_1 < d_0$, as illustrated in FIGS. 2A-2B) and the capacitance between the elements increases. As illustrated in FIGS. 2A-2B, as the fabric substrate 130 is stretched perpendicular to the length of the fingers (dimension 260), the gap between adjacent fingers of the elements increases (e.g., from $d_0$ to $d_2 > d_0$, as illustrated in FIGS. 2C-2D) and the capacitance between the elements decreases.

In such embodiments, and as illustrated in FIGS. 2A-2D, the first and second conductive elements 210 are configured to be capacitively coupled in response to applied electrical stimulus signals to the first and/or second elements. The first fabric layer comprises an electrically insulating fiber material. The first element comprises a first set of fingers 210-a interwoven into the first fabric layer along the long axis of the first conductive element (e.g., dimension 250), the first set of fingers 210-a physically and electrically connected by and extending along a first direction from a first base 210-c embroidered into the first fabric layer. The second element comprises a second set of fingers 210-b alternating with the first set of fingers 210-a and interwoven along the long axis of the first conductive element, the second set of fingers physically and electrically connected by and extending along a second direction from a second base 210-d embroidered into the first fabric layer, the second direction opposite and parallel to the first direction 211-a. In such embodiments, the first set of fingers 210-a are physically and electrically separated from the second set of fingers 210-b.

In such embodiments, the first signal represents an increase in capacitance between the interdigitated elements in response to a strain applied to the fabric substrate along lengths of the first and second sets of fingers. On the other hand, the first signal represents a decrease in capacitance between the interdigitated elements in response to a strain applied to the fabric substrate perpendicular to the lengths of the first and second sets of fingers. A measure of deformation (e.g., stretch) is computed based on the first signal based on the following equation:

$$\Delta C \cong \frac{\varepsilon_r + 1}{W} \Delta l [(n-3)*0.09 + 0.1] \quad (2)$$

$$\Delta C \cong \frac{\varepsilon_r + 1}{\Delta W} l [(n-3)*0.09 + 0.1] \quad (3)$$

where C is the capacitance measured, $\in_r$ is the relative permittivity of the insulating fabric layer, W is the total dimension of the base of the interdigital region in centimeters, l is the length of the digits in centimeters, and n is the number of digits.

In some embodiments, the first and second coupled conductive elements (210-$a$ and 210-$c$; and 210-$b$ and 210-$d$) are respectively encapsulated by a first and a second electrically insulating elastic fiber material coating configured to be interwoven amidst threads of the electrically insulating fiber material and configured to deform corresponding to deformation of the first and second elements. The electrically insulating encapsulation prevents electrical discharge/leakage/shorting when current or charge flows through the first and second elements, since the interdigitated elements, if formed on the surface of the fabric substrate, can come in contact with external conductive surfaces.

Figure 3A:
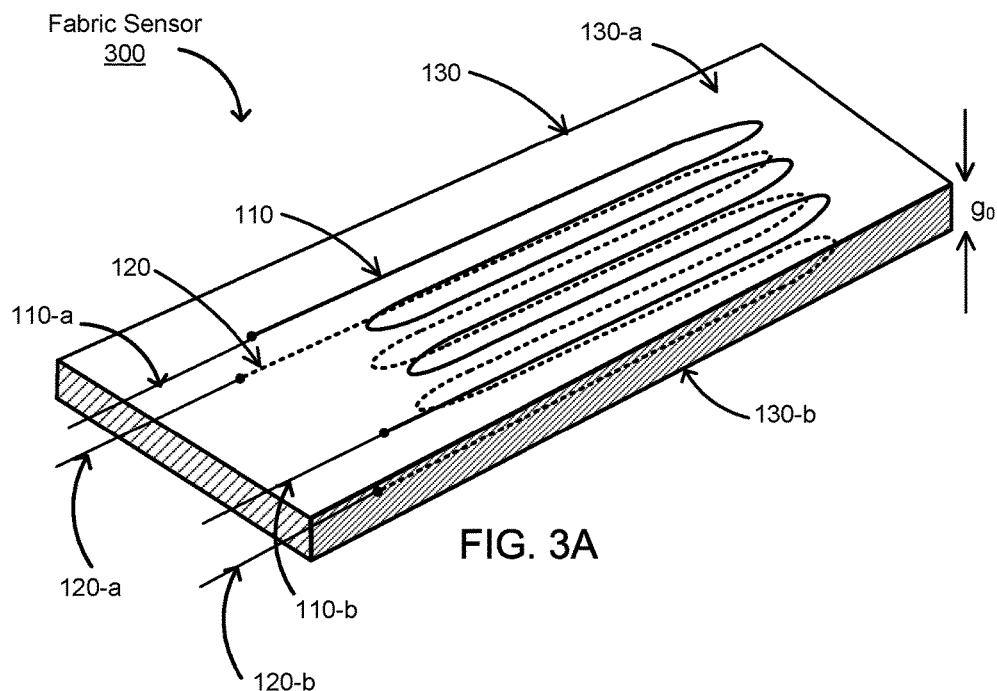
FIGS. 3A-3D illustrate views of fabric strain sensors having strain gauges embroidered into distinct layers of a multi-layer fabric substrate, in accordance with one or more embodiments.
Figure 3B:
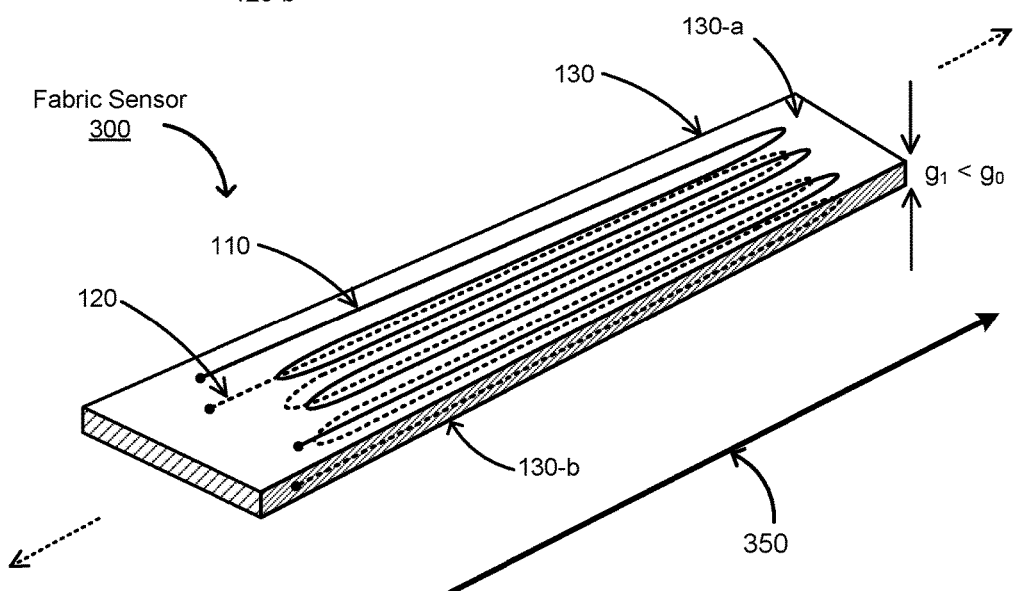
Figure 3C:
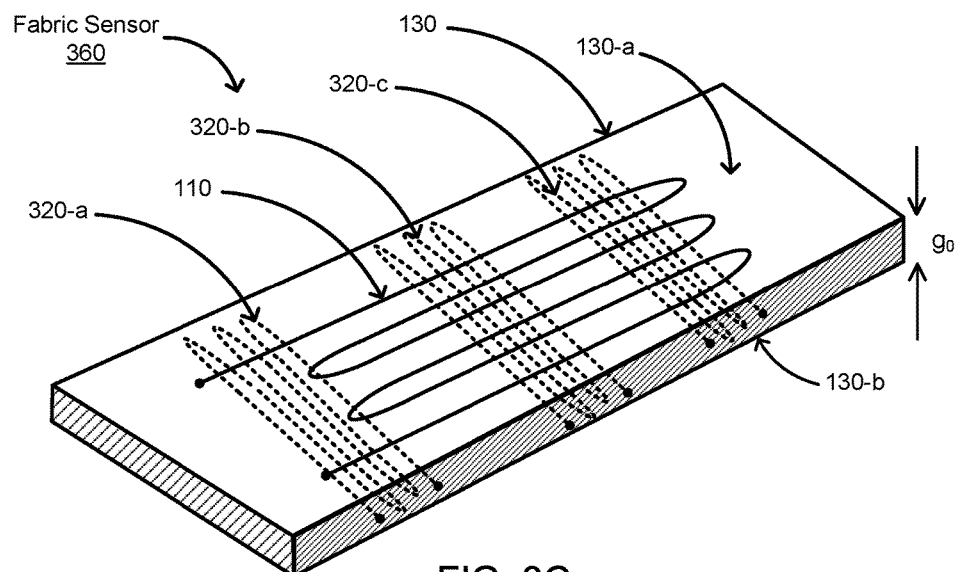
Figure 3D:
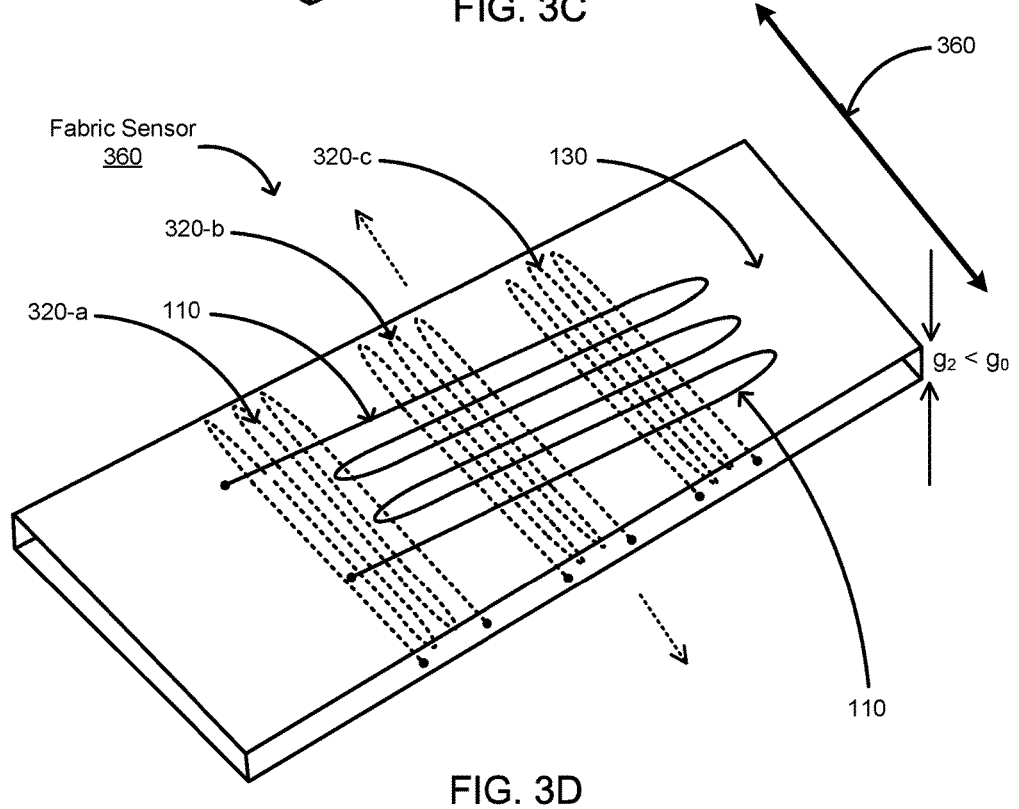

FIGS. 3A-3D illustrate views of fabric strain sensor 300 with strain gauges embroidered into a first surface 130-$a$ and a second surface 130-$b$ of a fabric substrate 130, in accordance with one or more embodiments. As illustrated in FIGS. 3A-3D, in some embodiments, conductive fabric traces are woven or embroidered, on top and bottom fabric layers 130-$a$ and 130-$b$ of a thick or multilayer fabric substrate 130. As the fabric is stretched, the total thickness of the fabric (g) is decreased (e.g., from $g_0$ to $g_1 < g_0$ as shown in FIGS. 3A-3B; or from $g_0$ to $g_2 < g_0$ as illustrated in FIGS. 3C-3D) which can be measured as an increase in capacitive coupling between the top and bottom conductive fabric traces 110 and 120.

As shown in FIG. 3A, a fabric sensor 300 includes a first strain gauge 110, a second strain gauge 120, and a fabric substrate 130. In some embodiments, the fabric substrate 130 is a multilayer fabric. The first strain gauge 110 is interwoven (intertwined, embroidered, or sewn) into a first fabric layer 130-$a$ of the fabric substrate 130. The second strain gauge 120 is interwoven (intertwined, embroidered, or sewn) into a second fabric layer 130-$b$ of the fabric substrate 130, the second surface 130-$b$ being separated from the first surface 130-$a$.

The first strain gauge 110 is configured to create (e.g., output an instrumented signal in response to a stimulating signal) a first signal in response to a strain applied in a first direction 350. In other words, the first strain gauge 110 can be interfaced to an instrument which stimulates the first strain gauge 110 appropriately so the instrument can measure a first electrical property as a first signal which changes in response to a first strain applied along a given axis of the first strain gauge. The second strain-gauge 120 is configured to create (e.g., provide or output an instrumented signal in response to a stimulating signal) a second signal in response to a strain applied in the same first direction 350. In some embodiments, the first and second strain-gauges are symmetrically formed on distinct layers of the multilayer fabric to have the same or symmetrically corresponding alignment, on the distinct layers of the fabric substrate. For example, the lengths (e.g., leads) of the first and second strain gauges are parallel (and optionally coincide and are co-planar). As a result, the first and second strain gauges provide like responses (resulting in the stimulus signal changing with the same polarity) to a strain applied in a specific direction (e.g., dimension 350). Thus, when a strain is applied along a direction parallel to a length of the strain gauges (e.g., dimension 350), both strain gauges output corresponding signals responsive to the strain. In other words, when a strain is applied along a direction parallel to a length of the strain gauges, the instrumentation system measures changes with the same polarity, resulting from changes in the gauge resistances.

Alternatively, and as illustrated in FIGS. 3C-3D, fabric sensor 360 includes a first strain-gauge 110 formed (e.g., interwoven) on a first fabric layer 130-$a$ of the fabric substrate 130, and one or more second strain-gauge elements 320-$a$, 320-$b$, and 320-$c$ formed (e.g., interwoven) on a second fabric layer 130-$b$ of the fabric substrate 130. The second strain-gauges 320-$a$, 320-$b$, and 320-$c$ are oriented along an orthogonal axis to the first strain-gauge 110; for example and respond to applied strain along a direction 360 (orthogonal to direction 350 illustrated in FIG. 3B) along lengths of the parallel leads of the second strain-gauges 320-$a$, 320-$b$, and 320-$c$.

In other words, in such embodiments, and as illustrated in FIGS. 3C-3D, the fabric substrate 130 further comprises a second fabric layer 130-$b$ and an electrically insulating interstitial layer formed between the first and second fabric layers. The interstitial layer is optionally the portion of the fabric substrate 130 formed between the first layer 130-$a$ and second layer 130-$b$, which optionally includes one or more intermediate layers of fabric or other material placed physically between the first and second fabric layers. In such embodiments, the deformation sensing fabric material further comprises a second conductive element (e.g., 320-$a$, 320-$b$, or 320-$c$ as illustrated in FIG. 3C) interwoven into threads of the second fabric layer 130-$b$. The second conductive element (e.g., 320-$a$ illustrated in FIG. 3C) is configured to output a second signal in response to a strain applied in a second direction (dimension 360), the second direction perpendicular to the first direction (e.g., dimension 350, explained with reference to FIGS. 3A-3B), the second direction along a long-axis of the second conductive element (e.g., along the length of the leads of strain gauge 320-$a$.

Returning to FIGS. 3A-3B, and as illustrated in FIG. 1A, and in some embodiments, the first strain-gauge element 110 has two distinct terminals, a first terminal 110-$a$ and a second terminal 110-$b$. The first signal output from the first strain gauge 110 is measurable across the first and second terminals of the first strain gauge 110. In some embodiments, the first signal is indicative of a first resistance (R1) or a first resistance change ($\Delta$R1) of the first strain gauge 110 measured in response to an applied deformation along direction 350. The deformation may occur in response to the applied strain in the first direction and other deformations (such as flexural or bending deformations).

In some embodiments, the second strain-gauge 120 has two distinct terminals, a third terminal 120-$a$ and a fourth terminal 120-$b$, as shown in FIG. 3A. The second signal is measurable across the third and fourth terminals of the second strain gauge 120. In some embodiments, the second signal is indicative of a second resistance (R2) or second resistance change ($\Delta$R2) of the second strain-gauge element 120 measured responsive to the applied deformation.

In some embodiments, the fabric substrate 130 comprises interstitial fabric layers of electrically-insulating dielectric fabric material. The deformation sensor 100 is configured to output a third signal responsive to the applied strain in the first direction 350, the third signal being measurable between a terminal of the first strain-gauge 110 and a terminal of the second strain-gauge 120. In some embodiments, the third signal is indicative of a capacitance (C) or capacitance change (ΔC) between the conductive elements of the strain gauges, measured responsive to the applied deformation.

As illustrated in FIGS. 3A-3B, the fabric sensor 300 includes the first and second strain-gauge 110 and 120 and the fabric substrate 130, as explained with reference to FIG. 1A. In some embodiments, and in the illustration of FIG. 3A, both the first and second strain-gauges 110 and 120 have a meandering shape, comprising one or more arcuate (e.g., curved or semi-circular) heads and a set of parallel elongate leads extending from ends of the arcuate heads.

In some embodiments, alignment of the outlines of the first and second strain-gauge elements lie in parallel congruent surfaces and are positioned in a manner that the projected area of one onto the other is maximized (aligned). For example, corresponding leads of the sets of elongate parallel leads of the first and second strain gauge 110 and 120 are respectively parallel and have substantially the same dimensions.

In some embodiments, a measure (e.g., an absolute metric or a fractional proportion) of stretch deformation and a measure (e.g., an absolute metric or a fractional proportion) of flex deformation of the fabric sensor 300, in the applied deformation, is computed based on the measured first signal from the first strain gauge 110, the measured second signal of the second strain-gauge 120, and the third signal.

In some embodiments, stretch deformation is determined as a strain on the strain-gauge element(s), computed as a change in length as a proportion of the original undeformed length [i.e., $(\Delta L_1 + \Delta L_2)/2L_0$; where $\Delta L_1$ and $\Delta L_2$ are changes in the lengths of the first and second strain-gauges 110 and 120 and $L_0$ is the original length, respectively or if $\Delta L_1 = \Delta L_2 = \Delta L$, then as $(\Delta L)/L_0$], expressed as a fraction or as a percentage. For example, a strain-gauge of an undeformed length of 10 cm stretched to 15 cm has undergone a strain of 50%. In some embodiments, the measure of stretch deformation is indicative of an average change in lengths of the first and second strain gauges 110 and 120. In such embodiments, the measure of stretch deformation, is computed based on the first, second, and third signals, using the formulas:

$$R_1 = R_0 + \Delta R_1 = R_0 + (GF \cdot \Delta L_1) \quad (4)$$

$$R_2 = R_0 + \Delta R_2 = R_0 + (GF \cdot \Delta L_2) \quad (5)$$

$$C = \varepsilon \frac{\text{Area}}{\text{gap}} = \varepsilon \frac{L_0 \cdot W_0}{g} = \varepsilon \frac{L_0 \cdot W_0}{(g_0 - \Delta L \cdot Y)} = \varepsilon \frac{L_0 \cdot W_0}{\left(g_0 - \left(\frac{\Delta L_1 + \Delta L_2}{2}\right)\right)} \quad (6)$$

where R1 is the first resistance, R2 is the second resistance, and C is the capacitance; and Area is an overlap between first and second strain-gauge elements, GF is a Gauge Factor relating strain and resistance, γ is a Poisson's Ratio of the fabric substrate relating deformations between axes, $L_0$ is an undeformed length of the first and second strain-gauge elements, $\Delta L, \Delta L_1, \Delta L_2$ are length changes of the first and second strain-gauge elements, $W_0$ is an undeformed length of the first and second strain-gauge elements, ∈ is a dielectric constant of the fabric substrate, $R_0$ is a baseline resistance of the first and second strain-gauge elements, and $g, g_0$ are, respectively, deformed and baseline widths of the fabric substrate.

Alternatively, if $\Delta L0.1 = \Delta L2 = \Delta L$, then:

$$R_1 = R_2 = R_0 + (GF \cdot \Delta L) \quad (7)$$

$$C_{stretch} = \varepsilon \frac{L_0 \cdot W_0}{g} = \varepsilon \frac{L_0 W_0}{g_0 - \left(\frac{\Delta L_1 - \Delta L_2}{2}\right) Y} = \varepsilon \frac{L_0 \cdot W_0}{g_0 - \Delta L \cdot Y} \quad (8)$$

In some embodiments, the measure of pure flex deformation is indicative of an angular bend of the surfaces of the fabric substrate 130 on which the first and second strain-gauges are formed. As one example, the measure of pure flex corresponds to a radius subtended by (e.g., average radius of curvature or bend radius for) the arcs formed due to bending of the surfaces on which the conductors are formed. In such embodiments, a measure of pure flex deformation, based on the first, second, and third signals, is computed using the formulas:

$$C_{bend} = C_0 \text{ because } g = g_0 \quad (9)$$

$$R_1 = R_0 + (GF \cdot \Delta L_1) \approx R_0 + \left(\frac{g}{2\rho_1} \cdot GF\right) \quad (10)$$

$$R_2 = R_0 + (GF \cdot \Delta L_2) \approx R_0 + \left(\frac{-g}{2\rho_2} \cdot GF\right) \quad (11)$$

where R1 is the first resistance, R2 is the second resistance, and $C_{bend}$ is the capacitance; and GF is a Gauge Factor relating strain and resistance of the first and second strain-gauge elements, Y is a Poisson's Ratio of the fabric substrate relating deformations between axes, $L_0$ is an undeformed length of the first and second strain-gauge elements, $\Delta L_1, \Delta L_2$ are length changes of the first and second strain-gauge elements, $R_0$ is a baseline resistance of the first and second strain-gauge elements, g, is a deformed width of the fabric substrate, and $\rho_1$ and $\rho_2$ are bend radii of the first and second surfaces of the fabric substrate.

For a case where stretch and flex deformations are combined (both present), and for a configuration where $C_{measured} \neq C_0$, the measures of stretch and flex deformation are computed based on calculating a common $\Delta L_{stretch}$ for both electrodes (using equation 7 and 8); subtracting from $R_{1_{measured}}$ and $R_{2_{measured}}$; and then calculating bend radii $\rho_1$ and $\rho_2$ (equations 10 and 11). For a combined stretched and bent configuration, a superposition of the two effects (stretch and flex) is considered. The total stretch is estimated based on the capacitance (or by proxy, the gap corresponding to the deformed width of the substrate (g)) of the elastic substrate. A new baseline length of the strain-gauge elements ($L_0'$) is computed (e.g., using equations 7 and 8). A new baseline measure of $R_1'$ and $R_2'$ are determined. The curvature (measure of flex) is computed based on a differences $L_1-L_0'$ and $L_2-L_0'$ (alternately represented by $R_1-R_1'$ and $R_2-R_2'$), for example, using the same method (e.g., equations 7 and 8) as described for pure curvature (flex).

Figure 4A:
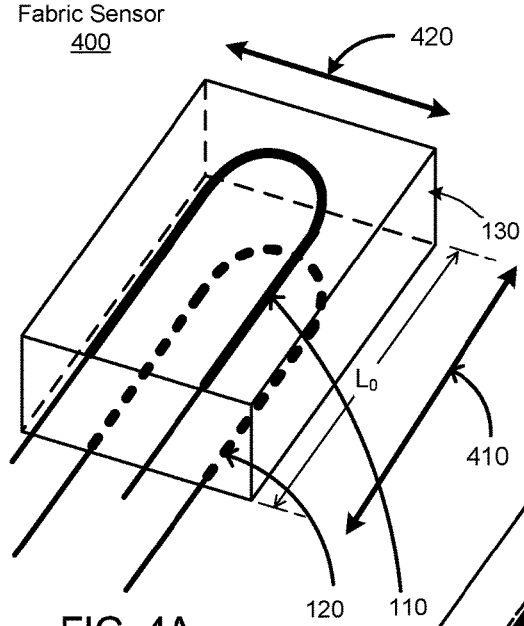
FIGS. 4A-4C illustrate length-wise stress deformations applied to a fabric strain sensor, according to one or more embodiments.
Figure 4B:
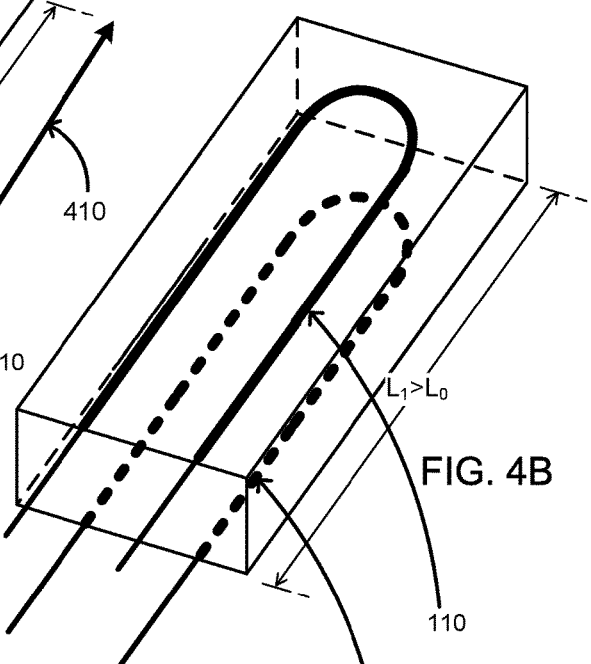
Figure 4C:
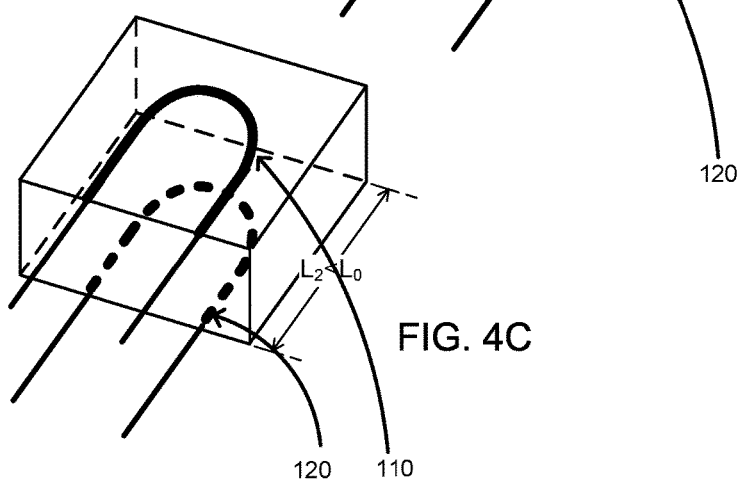

FIGS. 4A-4C illustrate length-wise stretch deformations (along direction/dimension 410) applied to a fabric strain sensor 400, according to one or more embodiments. FIGS. 5A-5C illustrate breadth-wise stress deformations (along direction/dimension 420) applied to a fabric sensor, according to one or more embodiments.

Fabric sensor 400 is analogous to sensor 300, but with a simplified geometry that has one arcuate head and a pair of elongate leads, for ease of illustration. The functional and operational description of sensor 400 herein is applicable to sensor 300.

FIG. 4A illustrates the fabric sensor 400 in the absence of any deformation. FIG. 4B illustrates an increase in length (and extension or elongation) of the fabric sensor 400 due to an applied stretch deformation. FIG. 4C conversely illustrates a decrease in length (a compression) of the deformation sensor 400 due to an applied stretch deformation.

FIG. 5A illustrates the fabric sensor 400 in the absence of any deformation. FIG. 5B illustrates an increase in breadth (and extension or elongation) of the deformation sensor 400 due to an applied stretch deformation. FIG. 5C conversely illustrates a decrease in breadth (a compression) of the fabric sensor 400 due to an applied stretch deformation.

In some embodiments, the fabric sensor 400 is less sensitive to deformation along the breadth-wise direction illustrated in FIGS. 5A-5C than along the length-wise direction illustrated in FIGS. 4A-4C. In such embodiments, to sense and disambiguate stretch along both the length-wise and breadth-wise directions (410 and 420), and as explained further with reference to FIGS. 3C-3D and 7A-7F, the deformation sensor optionally includes two pairs of strain-gauge elements, the two pairs aligned orthogonal to each other. For example, as shown in FIG. 7A, the primary strain-gauge pair 110-*a* and 120-*a* is perpendicular to the secondary pair 110-*b* and 120-*b*. In such embodiments, a direction of the stretch deformation (e.g., along the length of the primary pair of leads 110-*a* and 120-*a* as shown in FIG. 7A-7C), or along the lengths of the secondary pair of leads 110-*b* and 120-*b* as shown in FIG. 7A-7C) is determined based on the measured first, second, and third signals as obtained from both pairs—110-*a* and 120-*a*, as well as 110-*b* and 120-*b*. Thus, when coupled to this orthogonal U-pair configuration, bend directions can be disambiguated. The first strain-gauge pair (110-*a* and 120-*a*) would respond (via change in their respective resistances) to a deformation in a first bend (or stretch) direction along their respective lengths, whereas the second pair (110-*b* and 120-*b*) would be relatively unresponsive in this first bend (or stretch) direction. Conversely, the second strain-gauge pair (110-*b* and 120-*b*) would respond (via change in their respective resistances) to deformation in a second bend (or stretch) direction along their respective lengths, whereas the first pair (110-*b* and 120-*b*) would be unresponsive in this second bend (or stretch) direction.

Returning to the configurations of FIGS. 4A-4C and 5A-5C, in some embodiments, a magnitude of the stretch deformation is computed based on the measured first, second, and third signals; for example, as an average length change of the leads of the first or second strain-gauge elements, or a change in a distance between the leads of a given lead pair of the first or second gauge, based on the values of R1, R2, and C obtained from the first, second, and third signals.

For example, for a length-wise stretch (e.g., FIG. 4B), a magnitude of stretch is computed using the equations 4-8.

On the other hand, for a breadth-wise stretch (e.g., FIG. 5B), the magnitude of stretch is computed using the equations 6 and 8 (change in capacitance), since a change in resistances R1 and R2 would be negligible for a breadth-wise stretch.

Furthermore, the fabric sensor 400 is used to determine whether the stretch deformation corresponds to a compression stretch or an elongation stretch by comparing the measured first, second, and third signals. For example, a compression (e.g., FIG. 4C) would decrease lengths of the first and second strain-gauge elements 110 and 120 and increase the gap between the first and second strain-gauge elements 110 and 120, thus causing a change in resistances (R1 and R2) and a change in capacitance (C).

Figure 6A:
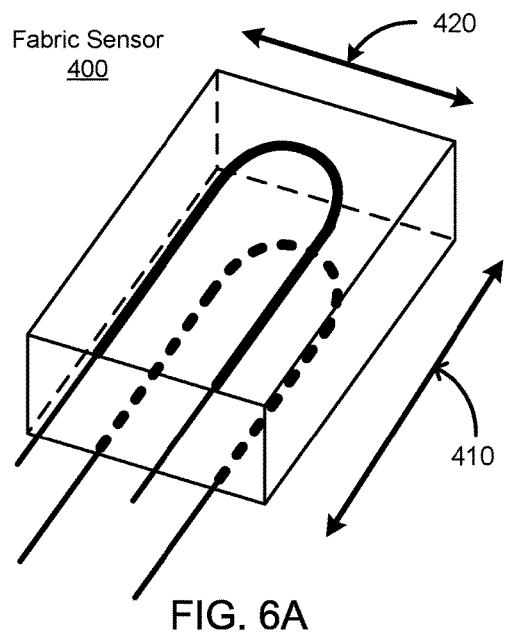
FIGS. 6A-6C illustrate length-wise flex deformations applied to a fabric strain sensor, according to one or more embodiments.
Figure 6B:
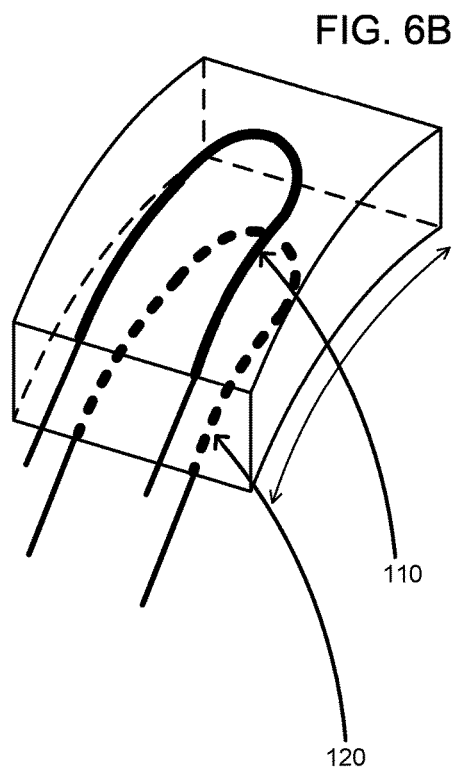
Figure 6C:
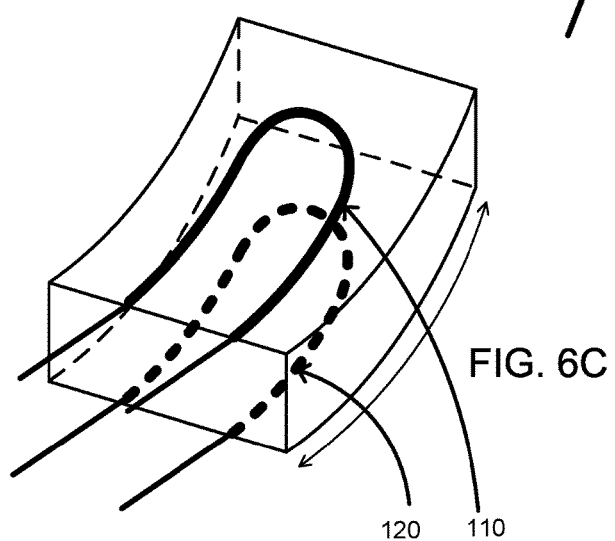

FIGS. 6A-6C illustrate length-wise flex deformations (along direction/dimension 410) applied to fabric sensor 400, according to one or more embodiments.

FIG. 6A illustrates the deformation sensor 100 in the absence of any deformations. FIG. 6B illustrates a length-wise flex deformation (bending along the length of the leads) of the fabric sensor 400 due to an applied flex deformation, the bending being toward the second element 120. FIG. 6C conversely illustrates a length-wise flex deformation (bending along the length of the leads) of the fabric sensor 400 due to an applied flex deformation, the bending being toward the first element 110.

FIGS. 7A-7C illustrate a first modified fabric sensor 700 including orthogonal strain-gauge pairs to detect and disambiguate stretch or flex deformations along two orthogonal directions 710 and 720 (e.g., length-wise versus breadth-wise deformations, respectively), according to one or more embodiments. For instance, the fabric sensor 700 includes two pairs of strain-gauge elements (the primary strain-gauge pair 110-*a* and 120-*a*; and the secondary pair 110-*b* and 120-*b*), the two pairs aligned orthogonal to each other and configured to generate respective signals in response to stretch and flex deformations along orthogonal directions (710 and 720, respectively).

FIG. 7A illustrates the deformation sensor 700 in the absence of any deformations. FIG. 7B illustrates a breadth-wise flex deformation (bending along direction/dimension 720 orthogonal to the length of the primary leads 110-*a* and 120-*a*, but along the lengths of the secondary leads 110-*b* and 120-*b*) of the fabric sensor 700 due to an applied flex deformation, the bending being toward the second element 120-*b*. FIG. 7C conversely illustrates a breadth-wise flex deformation (bending along direction/dimension 720 orthogonal to the length of the primary leads 110-*a* and 120-*a*, but along the lengths of the secondary leads 110-*b* and 120-*b*) of the deformation sensor 700 due to an applied flex deformation, the bending being toward the first element 110-*b*.

In some embodiments, when the fabric sensor includes orthogonal strain-gauge pairs (such as those illustrated in FIGS. 7A-7C), a direction of the flex deformation (e.g., whether the flex is along the length of the leads as shown in FIGS. 6A-6C, or perpendicular to the lengths of the primary leads and along the lengths of the secondary leads, as shown in FIGS. 7A-7C) is determined based on the measured first, second, and third signals independently obtained from each of the lead pairs.

Additionally, in some embodiments, a magnitude of the flex deformation is determined based on the first, second, and third signals (indicative of R1, R2, and C) independently obtained from each of the lead pairs. In some cases, the magnitude of flex corresponds to an average radius of curvature subtended by arcs formed by the bent surfaces of the fabric substrate that undergo bending due to the applied deformation. Alternatively, the magnitude of flex corresponds to an average angle subtended by arcs formed by the bent surfaces of the fabric substrate that undergo bending due to the applied deformation.

Stated differently, in some embodiments, a deformation sensing apparatus (e.g., first modified deformation sensor 700) comprises a fabric substrate 130, a first strain-gauge pair (e.g., primary pair of strain-gauges 110-*a* and 120-*a*), and a second strain-gauge pair (e.g., secondary pair of strain-gauges 110-*b* and 120-*b*).

The first strain-gauge pair comprises a first strain-gauge element 110-*a* formed (e.g., woven, embroidered, or otherwise intertwined) on a first surface of the fabric substrate 130, and configured to output a first signal (indicative of a resistance of the first strain-gauge element 110-*a*) in response to a strain applied in a first direction 710; and a second strain-gauge element 120-*a* formed on a second surface of the fabric substrate 130 opposite to the first surface, and configured to output a second signal (indicative of a resistance of the second strain-gauge 120-*a*) in response to a strain applied in the same first direction 710. The fabric sensor 750 is further configured to output a third signal (indicative of a capacitance of the fabric substrate 130 measured between the first and second strain-gauge elements 110-*a* and 120-*a*) responsive to an applied deformation, the third signal being measurable between a terminal of the first strain-gauge 110-*a* and a terminal of the second strain-gauge 120-*a*.

The second strain-gauge pair comprises a third strain-gauge element 110-*b* formed substantially on the first layer of the fabric substrate 130, and configured to output a fourth signal (indicative of a resistance of the third strain-gauge 110-*b*) in response to a strain applied in a second direction 720; and fourth strain-gauge 120-*b* formed substantially on the second layer of the fabric substrate 130 distinct from the first layer, and configured to output a fifth signal (indicative of a resistance of the fourth strain-gauge 120-*b*) in response to a strain applied in the same second direction 720. The fabric sensor 750 is configured to output a sixth signal (indicative of a capacitance of the fabric substrate 130 measured between the third and fourth strain gauges 110-*b* and 120-*b*) responsive to an applied deformation, the sixth signal being measurable between a terminal of the third strain-gauge 110-*b* and a terminal of the fourth strain-gauge 120-*b*.

In some embodiments, the first direction 710 is orthogonal to the second direction 720; the strain-gauge elements 110-*a* and 120-*a* of the first strain-gauge pair, and the strain-gauge elements 110-*b* and 120-*b* of the second strain-gauge pair are mutually orthogonal.

In such embodiments, a direction of stretch deformation is determined as being either a stretch in the first direction 710 or in the second direction 720 by comparing magnitudes of the first, second, fourth, and fifth signals detected from the first and second strain-gauge pairs. For a stretch in the first direction 710, a magnitude of stretch is computed using the first and second signals; and for a stretch in the second direction 720, the magnitude of stretch is computed using the fourth and fifth signals.

Additionally, in such embodiments, a direction of flex deformation is determined as being either a bend in the first direction 710 or in the second direction 720 by comparing magnitudes of the first, second, fourth, and fifth signals detected from the first and second strain-gauge pairs. For a bend in the first direction 710, a magnitude of bend is computed using the first and second signals; and for a bend in the second direction 720, a magnitude of bend is computed using the fourth and fifth signals.

In such embodiments, for a length-wise bending arc (along lengths of the primary pair 110-*a* and 120-*a*), the magnitude of flex is computed using the equations 9-11 as applied to the first, second, and third signals obtained from the primary pair of strain-gauges 110-*a* and 120-*a*.

Conversely, for a breadth-wise bending arc (along lengths of the secondary pair 110-*b* and 120-*b*, as illustrated in FIGS. 7B-7C), the magnitude of flex is computed using the equations 9-11 as applied to the fourth, fifth, and sixth signals obtained from the secondary pair of strain-gauges 110-*b* and 120-*b*.

Additionally, the fabric sensor 750 can be used to determine, by comparing the measured first, second, and third signals from the appropriate pair of strain-gauges (110-*b* and 120-*b*, in the case of FIGS. 7A-7C), whether the flex deformation corresponds to a bend toward the first surface of the elastic substrate (toward 110-*b*) or a bend toward the second surface of the elastic substrate (toward 120-*b*). For example, for a flex toward the first surface of the substrate, a resistance R1 would be decreased (decrease in length of element 110-*b*) and resistance R2 would increase (increase in length of element 120-*b*).

Similarly, for the configuration 700 of FIGS. 7A-7C, for a length-wise stretch, a magnitude of stretch may be computed using the equations 4-8 as applied to signals measured from the primary strain-gauge pair 110-*a* and 120-*a* (e.g., the first, second, and third signals).

On the other hand, for a breadth-wise stretch, the magnitude of stretch is computed using the equations 4-8 as applied to signals measured from the secondary strain-gauge pair 110-*b* and 120-*b* (e.g., the fourth, fifth, and sixth signals).

FIGS. 7D-7F illustrate a second modified fabric sensor 750 including orthogonal strain-gauge elements (110-*b* and 120-*a*) to detect and disambiguate stretch or flex deformations along two orthogonal directions 710 and 720 (e.g., length-wise versus breadth-wise deformations), according to one or more embodiments.

Fabric sensor 750 is analogous to sensor 360 (as explained with reference to FIGS. 3C-3D), but with a simplified geometry that has one arcuate head and a pair of elongate leads, for each strain gauge element, for ease of illustration. The functional and operational description of sensor 750 herein is applicable to sensor 360.

In such embodiments, a fabric sensor (e.g., the second modified deformation sensor 750) comprises a multilayer fabric substrate 130, a first strain-gauge element 110-*b* formed (e.g., embroidered) on a first layer of the fabric substrate 130, and configured to output a first instrumented signal responsive to a stimulus signal (indicative of a resistance of the first strain-gauge element 110-*b*) in response to a strain applied in a first direction 710; and a second strain-gauge element 120-*a* formed on a second layer of the fabric substrate 130 opposite to the first layer, and configured to output a second instrumented signal responsive to a stimulus signal (indicative of a resistance of the first strain-gauge element 120-*a*) in response to a strain applied in a second direction 720. The fabric sensor 750 is configured to output a third signal (indicative of a capacitance of the fabric substrate 130 measured between the first and second strain-gauge elements 110-*b* and 120-*a*) responsive to an applied deformation, the third signal being measurable between a terminal of the first strain-gauge element 110-*b* and a terminal of the second strain-gauge element 120-*a*. The first direction 710 is orthogonal to the second direction 720. The first strain-gauge element 110-*b* and the second strain-gauge element 120-*a* are mutually orthogonal.

In such embodiments, a direction of stretch deformation is determined as being either a stretch in the first direction 710 or in the second direction 720 by comparing magnitudes of the first and second signals detected from the first and second strain-gauge elements 110-*b* and 120-*a*. For a stretch in the first direction 710, a magnitude of stretch is computed using the first and third signals; and for a stretch in the second direction 720, the magnitude of stretch is computed using the second and third signals.

For example, for a stretch in the first direction 710, a magnitude of stretch may be computed using the equations 4-8 as applied to signals measured from the second and third signals measured from the first and second strain-gauge elements 110-*b* and 120-*a*.

On the other hand, for a stretch in the second direction 720, the magnitude of stretch is computed using the equations 4-8 as applied to signals measured from the second and third signals measured from the first and second strain-gauge elements 110-*b* and 120-*a*.

Additionally, a direction of flex deformation is determined as being either a bend in the first direction 710 or in the second direction 720 by comparing magnitudes of the first and second signals detected from the first and second strain-gauge elements 110-*b* and 120-*a*. For a bend in the first direction 710, a magnitude of bend is computed using the first and third signals; and for a bend in the second direction 720, a magnitude of bend is computed using the second and third signals.

For example, for a bending arc along the first direction 710 (along lengths of the leads of the first strain-gauge element 110-*b*, as illustrated in FIGS. 7B-7C), the magnitude of flex may be computed using the equations 6-8 as applied to the first and third signals obtained from the first and second strain-gauges 110-*b* and 120-*a*.

Conversely, for a bending arc along the second direction 720 (along lengths of the leads of the second strain-gauge element 120-*a*), the magnitude of flex is computed using the equations 6-8 as applied to the second and third signals obtained from the first and second strain-gauges 110-*b* and 120-*a*.

FIGS. 8-11 illustrate examples of wearable systems that include one or more fabric sensors, according to one or more embodiments.

In one or more embodiments, a wearable device or system comprises one or more fabric sensors (such as those explained with reference to FIGS. 1-7). The wearable device or system may also include the measurement circuit and deformation analyzer (explained with reference to FIGS. 12A-12B). Alternatively, the wearable device may include the deformation sensor (and optionally the measurement circuit) and the first, second, and third signals may be sent to a remote (e.g., non-wearable) system or device; the remote system or device may include the measurement circuit and/or the deformation analyzer. In some embodiments, the first, second, and third signals are converted to preprocessed intermediate set of signals to be relayed to a remote system.

In some embodiments, each of the first and second strain-gauge elements of the fabric sensor within the wearable device has a meandering shape comprising one or more arcuate heads and one or more pairs of elongate leads extending from ends of the arcuate heads (as explained with reference to FIGS. 1A-1B). In such embodiments, alignment of the shapes of the first and second strain-gauge elements correspond and these aligned shapes are configured to circumscribe or surround an articulating joint. As a result, when the wearable device is positioned or worn around or in the vicinity of the joint, a movement of the joint results in a corresponding deformation of the deformation sensor and a generation of the first, second, and third signals responsive to the deformation. Then, using the approaches described herein, a measure of stretch deformation and flex deformation of the joint can be determined based on the first, second, and third signals.

Figure 8:
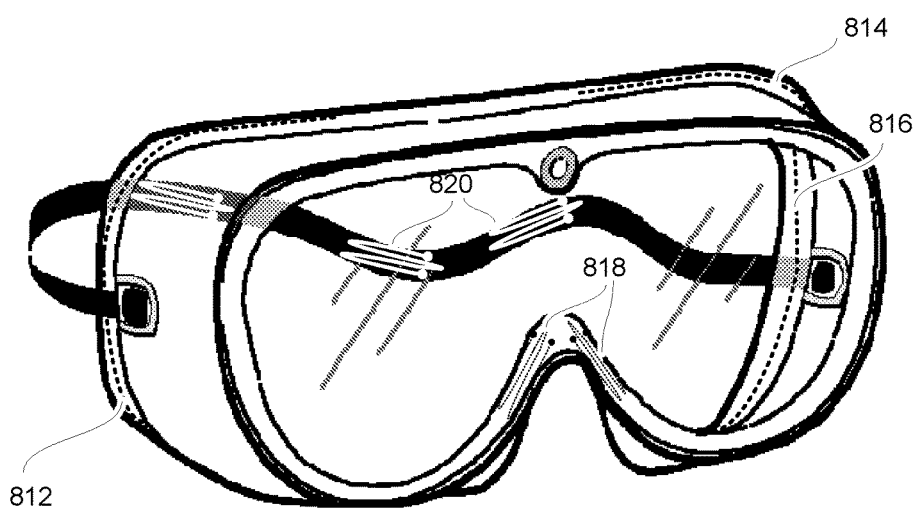
FIGS. 8-11 illustrate examples of wearable systems that include one or more deformation sensing fabrics, according to one or more embodiments.
Figure 9:
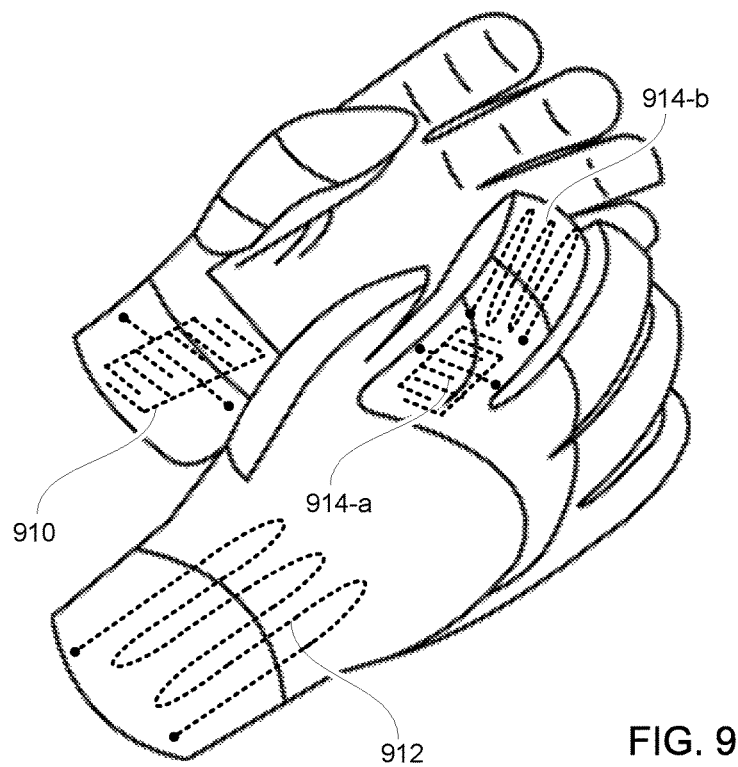
Figure 10:
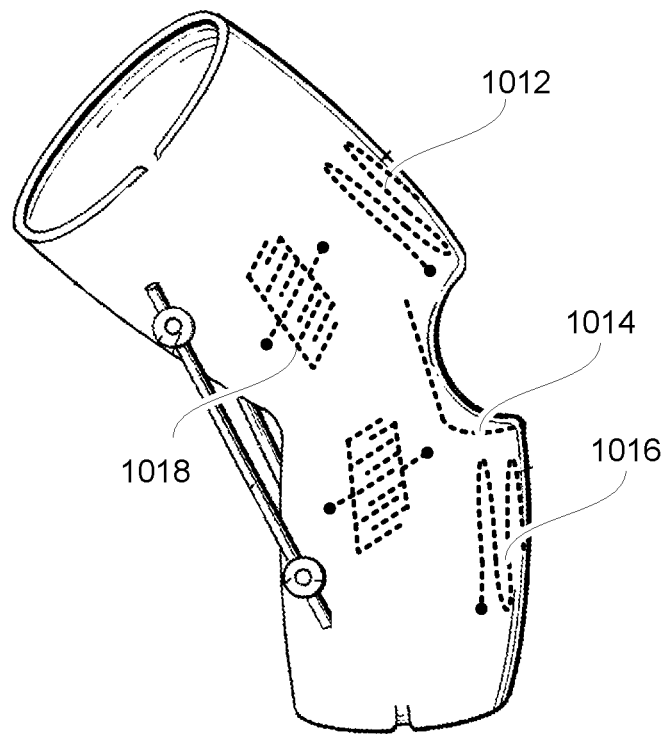

In some embodiments, the wearable device is a pair of goggles or a wearable headset (e.g., in FIG. 8) to be worn around a portion of the face. Correspondingly, the strain-gauges 812, 814, 816 are arranged to be substantially concentric with (circumscribing) sockets of the eyes or aligned with portions of the forehead and cheek bone as shown in FIG. 8, thus sensing movements of these parts for disambiguation. In some embodiments, one or more strain gauges 818 are provided in the nose pad in the goggles or wearable headset. In some embodiments, one or more strain gauges 820 are provided in the elastic headband of the goggles or wearable headset.

In some embodiments, the wearable device is a glove (e.g., in FIG. 9) to be worn around the hand or a cover (e.g., thimble or guard band) to be worn over a finger or wrist. Correspondingly, the embroidered strain gauge or capacitive sensor is arranged to be substantially concentric with joints of one or more fingers (914-*a*, 914-*b*) or the wrist joint (910 and 912) when the device is worn around the fingers or wrist. Alternatively or in addition, the fabric embroidered strain gauge or capacitive sensor is arranged to be above, below, on a side of the joint, or remotely coupled with a linkage (e.g., with an elastic string or tendon).

In some embodiments, the wearable device is a brace (e.g., in FIG. 10) to be worn over a knee, elbow, ankle, or shoulder joint. Correspondingly, the fabric strain-gauge or capacitive strain sensor may be arranged to be substantially concentric with the knee (1014), elbow, ankle, or shoulder joint. Alternatively, or in addition, the embroidered strain gauge or capacitive sensor may be arranged to be above (1012), below (1016), or on a side (1018) of the joint.

Figure 11:
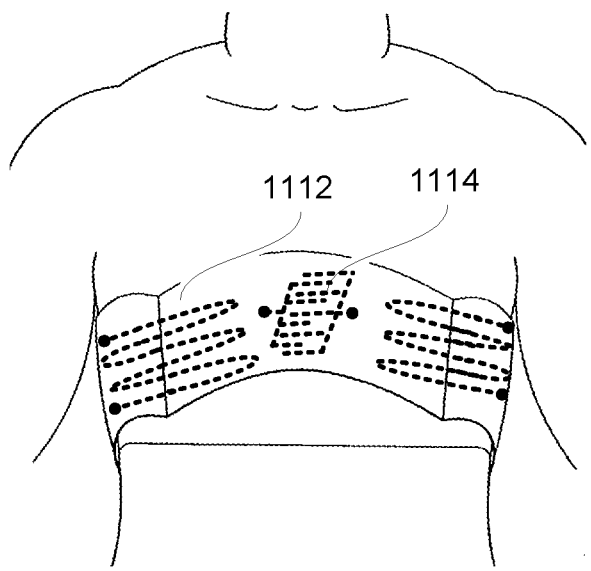

In some embodiments, the wearable device is a support brace to be worn over a neck or torso part (e.g., chest, back, or waist; as shown in FIG. 11). Correspondingly, the embroidered fabric strain gauge or capacitive sensor is arranged to be follow a contour of the neck or torso part (e.g., 1112 or 1114).

Figure 12A:
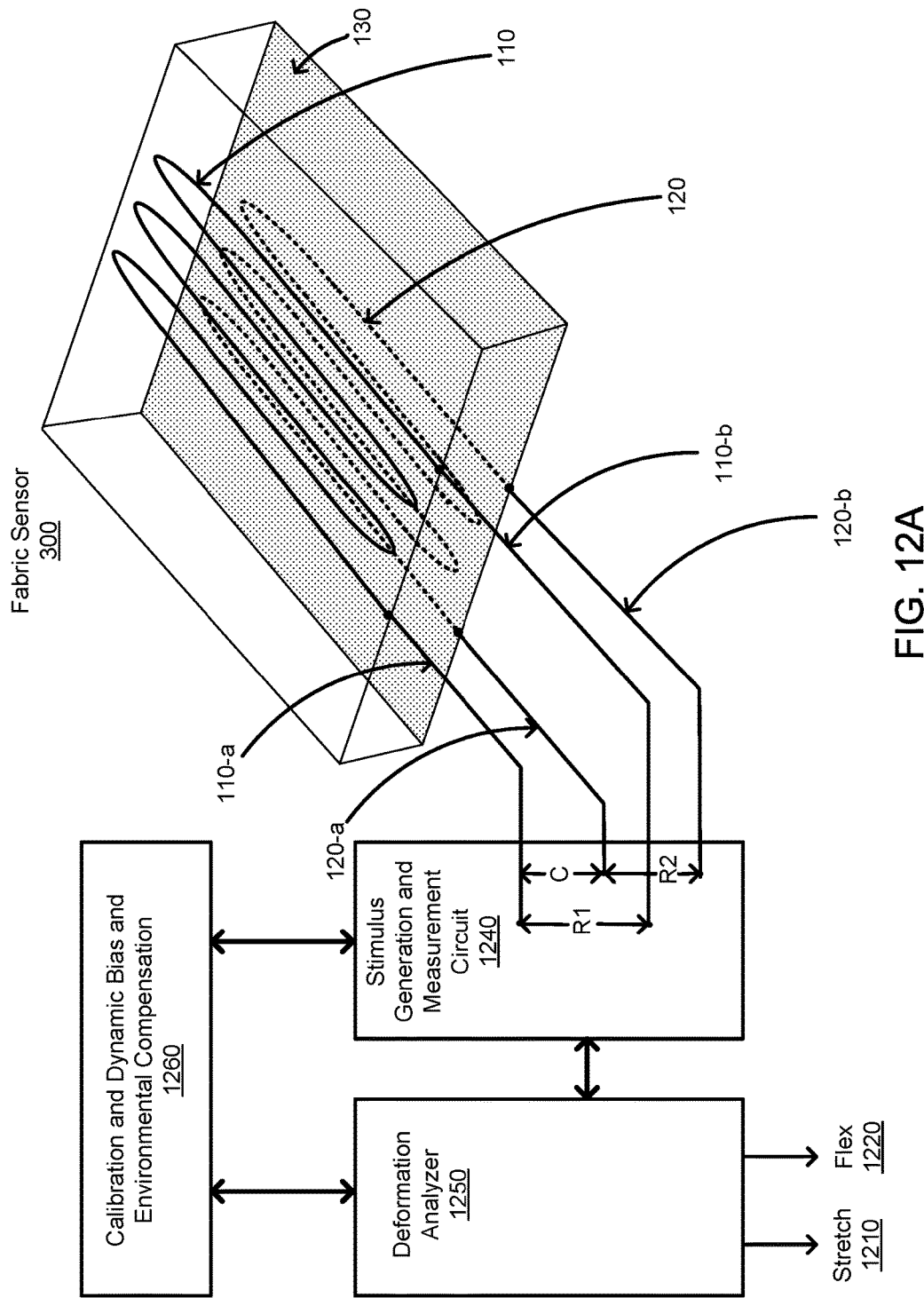
FIGS. 12A-12B illustrate a deformation sensing system including one or more deformation sensing fabrics, according to one or more embodiments.
Figure 12B:
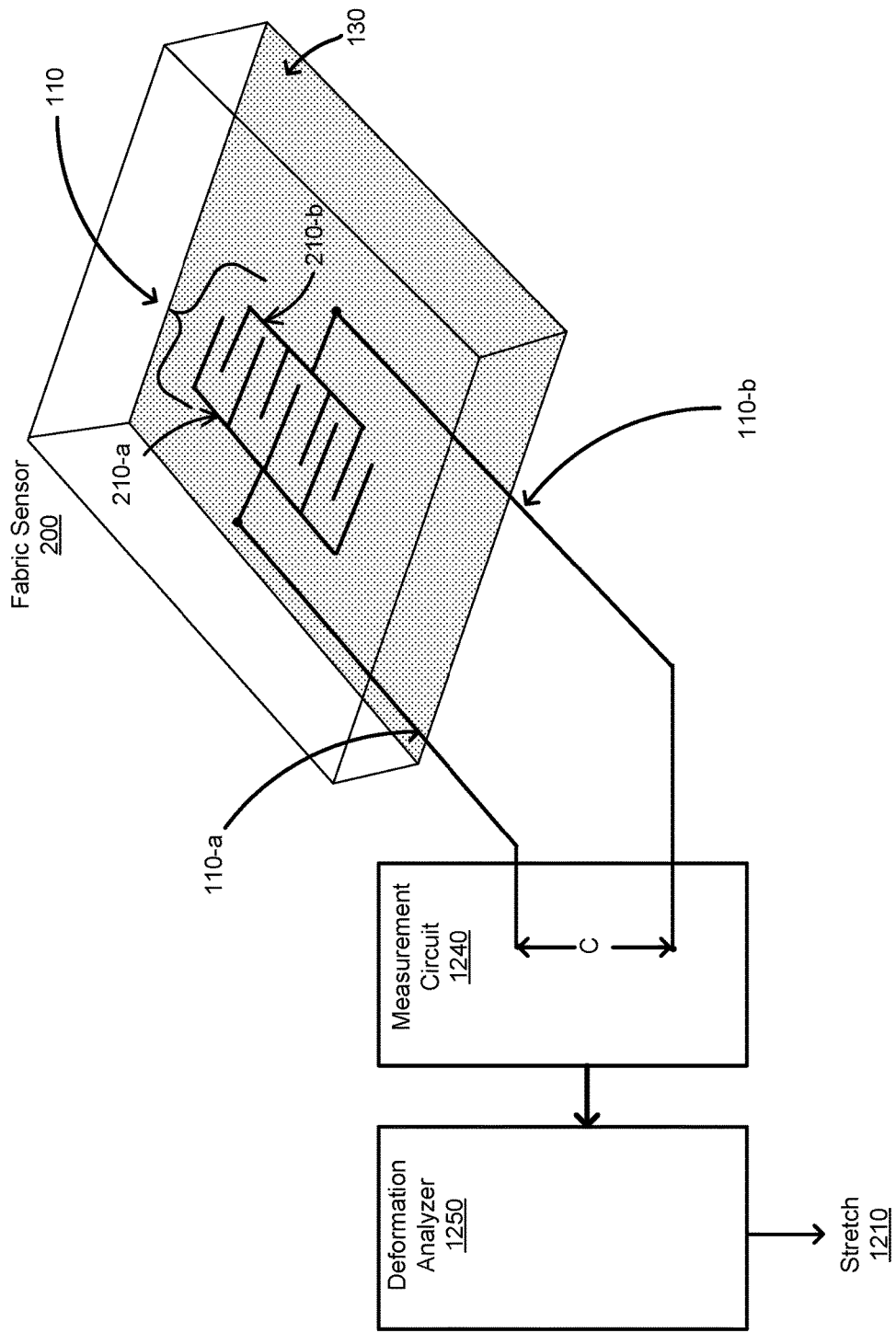

FIGS. 12A-12B illustrate a deformation sensing system 1200 including a fabric sensor (e.g., fabric sensor 300 in FIG. 12A; and fabric sensor 200 in FIG. 12B), according to one or more embodiments. In some embodiments, the deformation sensing system 1200 comprises a stimulus generation and measurement circuit 1240, a deformation analyzer 1250, and a calibration and dynamic bias and environmental compensation unit 1260.

In some embodiments, the stimulus generation and measurement circuit 1240 is configured to measure the first signal using the first strain-gauge element 110 and, optionally, the second signal using the second strain-gauge element 120 to determine an applied deformation. The stimulus generation and measurement circuit 1240 may combine measurements using a physical model so as to determine a more accurate estimated deformation or project such an estimate with reduced latency.

The stimulus generation and measurement circuit 1240 optionally generates stimulus and/or bias signals that enable measurement of the first and/or second signals from the first and/or second strain-gauge elements.

As explained with reference to FIGS. 3A-3B, in some embodiments, the first signal is indicative of a first resistance (R1) or a first resistance change (ΔR1) of the first strain-gauge element 110 measured responsive to an applied deformation (e.g., that includes the strain in the first direction). In some embodiments, the first signal is measured responsive to a first known electrical signal (e.g., known voltage or current) applied by the stimulus generation and measurement circuit 1240 between the first and second terminals 110-*a* and 110-*b* of the first strain-gauge element 110.

In some embodiments, and as explained with reference to FIGS. 3A-3B, the second signal is indicative of a second resistance (R2) or second resistance change (ΔR2) of the second strain-gauge element 120 measured responsive to the applied deformation. In some embodiments, the second signal is measured responsive to a second known electrical signal (e.g., known voltage or current) applied by the stimulus generation and measurement circuit 1240 between the third and fourth terminals 120-*a* and 120-*b* of the second strain-gauge element 120.

In some embodiments, the third signal is indicative of a capacitance (C) or capacitance change (ΔC) between the elements measured responsive to the applied deformation. In some embodiments, the third signal is measured responsive to a third known electrical parameter (e.g., a known alternating current frequency) used to create the stimulus used for the capacitance measurement or which could impact the capacitance measurement or is a parameter for the effective capacitance itself, such as frequency.

In some embodiments, the stimulus generation and measurement circuit 1240 has two alternating (time-interleaved) measurement phases. During a first phase, for measurement of R1 and R2, a known voltage or current may be provided across each of the first and second strain-gauge elements. During a second phase, for measurement of C, the first and second terminals 110-*a* and 110-*b* of the first strain-gauge element may be shorted to form one electrode of a capacitor and similarly, the third and fourth terminals 120-*a* and 120-*b* of the second strain-gauge element 120 may be shorted to form a second electrode of the capacitor; the elastic substrate forming the dielectric insulator between the first and second plates. The capacitance C is then optionally measured between the first plate (the first and second terminals 110-*a* and 110-*b*, shorted together) and the second plate (the third and fourth terminals 120-*a* and 120-*b*, shorted together).

The deformation analyzer 1250 is configured to determine attributes of the applied deformation (stretch 1210 and/or flex 1220) based on the measured first, second, and/or third signals. For example, the deformation analyzer 1250 is configured to determine for an applied a direction of stretch, direction of flex, measure (e.g., magnitude or proportion) of stretch, measure (e.g., magnitude or proportion) of flex, or any combination thereof, as described with reference to FIGS. 4-7.

Calibration and dynamic bias and environmental compensation unit 1260 provides a feedback path for the stimulus generation and measurement circuit 1240 to modify the stimulus and/or bias signal to be adjusted or modified based on the measured first and/or second signals or based on deformation measures computed based on the measured signals.

FIG. 12B illustrates the deformation sensing apparatus including fabric sensor 200 including an interdigitated capacitor embroidered into a fabric surface, as explained with reference to FIGS. 2A-2D.

In such embodiments, the stimulus generation and measurement circuit 1240 is configured to measure the first signal corresponding to a capacitance (C) measured across the interdigitated elements (210-*a* and 210-*b*) of the conductive element 110 in response to the applied deformation, and the deformation analyzer 1250 is further configured to compute the measure of stretch 1210 of the deformation sensing fabric, in the applied deformation, based on the measured capacitance.

In some embodiments, the first signal (the capacitance, C) is measured responsive to a first known electrical parameter (e.g., known voltage or current) of the stimulus applied by the stimulus generation and measurement circuit 1240 between the first and second electrodes 210-*a* and 210-*b*.

SUMMARY

The foregoing description of the embodiments has been presented for the purpose of illustration; it is not intended to be exhaustive or to limit the embodiments to the precise forms disclosed. Persons skilled in the relevant art can appreciate that many modifications and variations are possible in light of the above disclosure.

Some portions of this description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Some embodiments may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Some embodiments may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the embodiments be limited not by this detailed description, but rather by any claims that issue on an application based hereon. Accordingly, the disclosure of the embodiments is intended to be illustrative, but not limiting, of the scope of the embodiments, which is set forth in the following claims.

What is claimed is:

1. A deformation sensing fabric comprising:
   a fabric substrate comprising a first fabric layer;
   a first conductive element woven into the first fabric layer, and configured to:
      form a first strain gauge that outputs a first instrumented signal indicative of a measure of change in resistance of the first strain gauge in response to a strain applied to the fabric substrate along a length of the first strain gauge, and
      output the first instrumented signal, responsive to an applied stimulus signal;
   the first strain gauge comprises a meandering pattern of electrically conductive elastic yarn interwoven in the first fabric layer;
   the meandering interwoven pattern comprises one or more arcuate heads and a plurality of parallel elongate leads extending from ends of the one or more arcuate heads, the parallel leads formed along the length of the first strain gauge;
   the meandering interwoven pattern of electrically conductive elastic yarn forms a continuous electrically conductive path;
   the first strain-gauge has two distinct terminals, a first terminal and a second terminal, formed at two ends of the continuous electrically conductive yarn; and
   the first instrumented signal is measurable across the first and second terminals of the first strain-gauge.

2. A deformation sensing fabric comprising:
   a fabric substrate comprising a first fabric layer; and
   a first conductive element woven into the first fabric layer, and configured to output a first instrumented signal, responsive to an applied stimulus signal, indicative of a measure of change in an electrical property of the first conductive element in response to a strain applied to the fabric substrate along a long-axis of the first conductive element, and
   the first fabric layer comprises an electrically insulating fiber material;
   the first conductive element is configured to form a plurality of interdigitated coupled elements of a capacitor, including:
      a first coupled element comprising a first set of fingers interwoven into the first fabric layer along the long axis of the first conductive element, the first set of fingers physically and electrically connected by and extending along a first direction from a first base embroidered into the first fabric layer, and
      a second coupled element capacitively coupled to the first coupled element with a second set of fingers alternating with the first set of fingers and interwoven along the long axis of the first conductive element, the second set of fingers physically and electrically connected by and extending along a second direction from a second base embroidered into the first fabric layer, the second direction opposite and parallel to the first direction, the first set of fingers physically and electrically separated from the second set of fingers.

3. The deformation sensing fabric of claim 2, wherein:
   the first instrumented signal represents an increase in capacitance between the interdigitated coupled elements in response to a strain applied to the fabric substrate along lengths of the first and second sets of fingers; and
   the first instrumented signal represents a decrease in capacitance between the interdigitated coupled elements in response to a strain applied to the fabric substrate perpendicular to the lengths of the first and second sets of fingers.

4. The deformation sensing fabric of claim 2, wherein the first and second coupled elements are encapsulated by a first and a second electrically insulating elastic fiber material coating configured to be interwoven amidst threads of the electrically insulating fiber material and configured to deform corresponding to deformation of the first and second coupled elements.

5. A deformation sensing fabric comprising:
   a fabric substrate comprising a first fabric layer that comprises a first electrically insulating fiber material;
   a first conductive element woven into the first fabric layer, and configured to:
      form a first strain gauge, first strain gauge comprises a first electrically conductive elastic fiber material interwoven amidst threads of the first electrically insulating fiber material, and
      output the first instrumented signal, responsive to an applied stimulus signal, the first instrumented signal is indicative of a change in resistance of the first strain gauge in response to a strain applied to the fabric substrate along a length of the first strain gauge;
   the fabric substrate further comprises a second fabric layer comprising a second electrically insulating fiber material and an electrically insulating interstitial layer formed between the first and second fabric layers;
   the deformation sensing fabric further comprises a second conductive element interwoven into threads of the second fabric layer, the second conductive element configured to output a second instrumented signal in response to a strain applied in the same first direction;
   the second conductive element is configured to form a second strain gauge and the second instrumented signal is indicative of a change in resistance of the second strain gauge in response to a strain applied to the fabric substrate along a length of the second strain gauge; and
   the second strain gauge comprises a second electrically conductive elastic fiber material interwoven amidst threads of the second electrically insulating fiber material.

6. The deformation sensing fabric of claim 5, wherein the first and second strain gauges are encapsulated by a first and a second electrically insulating elastic fiber material coating configured to be interwoven respectively into the first and second fabric layers and configured to deform corresponding to respective deformation of the first and second strain gauges.

7. The deformation sensing fabric of claim 5, wherein:
the first strain-gauge comprises a first continuous electrically conductive yarn with two distinct terminals, a first terminal and a second terminal, formed at two ends of the first continuous electrically conductive yarn;
the first instrumented signal is a resistance measurement across the first and second terminals of the first strain-gauge;
the second strain-gauge element comprises a second continuous electrically conductive yarn with two distinct terminals, a third terminal and a fourth terminal, formed at two ends of the second continuous electrically conductive yarn; and
the second instrumented signal is a resistance measurement across the third and fourth terminals of the second strain-gauge.

8. A deformation sensing fabric comprising:
a fabric substrate comprising a first fabric layer that comprises a first electrically insulating fiber material;
a first conductive element woven into the first fabric layer, and configured to:
 form a first strain gauge that comprises a first electrically conductive elastic fiber material interwoven amidst threads of the first electrically insulating fiber material, and
 output a first instrumented signal, responsive to an applied stimulus signal, and the first instrumented signal is indicative of a change in resistance of the first strain gauge in response to a strain applied to the fabric substrate along a length of the first strain gauge;
the fabric substrate further comprises a second fabric layer and an electrically insulating interstitial layer formed between the first and second fabric layers;
the deformation sensing fabric material further comprises a second conductive element interwoven into threads of the second fabric layer, the second conductive element configured to output a second instrumented signal in response to a strain applied in a second direction, the second direction perpendicular to the first direction, the second direction along a long-axis of the second conductive element; and
the second conductive element is configured to form a second strain gauge and the second instrumented signal represents a change in resistance of the second strain gauge in response to a strain applied to the fabric substrate along a length of the second strain gauge.

9. A deformation sensing apparatus comprising:
deformation sensing fabric including:
 a fabric substrate comprising a first fabric layer that comprises a first electrically insulating fiber material, and
 a first conductive element woven into the first fabric layer, and configured to:
  form a first strain gauge and a first instrumented signal is indicative of a change in resistance of the first strain gauge in response to a strain in the applied deformation applied to the fabric substrate along a length of the first strain gauge,
  output the first instrumented signal, responsive to an applied stimulus signal;
a measurement circuit configured to measure the first instrumented signal from the first conductive element in response to an applied deformation;
a deformation analyzer configured to compute a measure of stretch of the deformation sensing fabric, in the applied deformation, based on the measured first instrumented signal from the first conductive element;
the fabric substrate further comprises a second fabric layer comprising a second electrically insulating fiber material and an electrically insulating interstitial layer formed between the first and second fabric layers;
the deformation sensing fabric further comprises a second conductive element interwoven into threads of the second fabric layer, the second conductive element configured to output a second instrumented signal in response to a strain in the applied deformation in the same first direction;
the second conductive element is configured to form a second strain gauge and the second instrumented signal is indicative of a change in resistance of the first strain gauge in response to a strain applied to the fabric substrate along a length of the first strain gauge;
the measurement circuit is further configured to measure the second instrumented signal from the second conductive element in response to the applied deformation, and a third instrumented signal between the first and second conductive elements indicative of a capacitance of the interstitial layer; and
the deformation analyzer is further configured to compute the measure of stretch and a measure of flex deformation of the deformation sensing fabric, in the applied deformation, based on the measured second and third instrumented signals.

10. A deformation sensing apparatus comprising:
deformation sensing fabric including:
 a fabric substrate comprising a first fabric layer that comprises a first electrically insulating fiber material, and
 a first conductive element woven into the first fabric layer, and configured to:
  form a first strain gauge and a first instrumented signal is indicative of a change in resistance of the first strain gauge in response to a strain in the applied deformation applied to the fabric substrate along a length of the first strain gauge,
  output the first instrumented signal, responsive to an applied stimulus signal;
a measurement circuit configured to measure the first instrumented signal from the first conductive element in response to an applied deformation;
a deformation analyzer configured to compute a measure of stretch of the deformation sensing fabric, in the applied deformation, based on the measured first instrumented signal from the first conductive element;
the fabric substrate further comprises a second fabric layer comprising a second electrically insulating fiber material and an electrically insulating interstitial layer formed between the first and second fabric layers;
the deformation sensing fabric further comprises a second conductive element interwoven into threads of the second fabric layer, the second conductive element configured to output a second instrumented signal in response to a strain in the applied deformation in second direction, the second direction perpendicular to the first direction, the second direction along a long-axis of the second conductive element;
the second conductive element is configured to form a second strain gauge and the second signal is indicative of a change in resistance of the second strain gauge in response to a strain applied to the fabric substrate along a length of the second strain gauge;

the measurement circuit is further configured to measure the second instrumented signal from the second conductive element in response to the applied deformation, and a third instrumented signal between the first and second conductive elements indicative of a capacitance of the interstitial layer; and the deformation analyzer is further configured to compute the measure of stretch and a measure of flex deformation of the deformation sensing fabric, in the applied deformation, based on the measured second and third signals.

11. A deformation sensing apparatus comprising:
deformation sensing fabric including:
　a fabric substrate comprising a first fabric layer, and
　a first conductive element woven into the first fabric layer, and configured to output a first instrumented signal, responsive to an applied stimulus signal, indicative of a change in an electrical property of the first conductive element in response to a strain applied to the fabric substrate along a long-axis of the first conductive element;
a measurement circuit configured to measure the first instrumented signal from the first conductive element in response to an applied deformation;
a deformation analyzer configured to compute a measure of stretch of the deformation sensing fabric, in the applied deformation, based on the measured first instrumented signal from the first conductive element;
the first fabric layer comprises an electrically insulating fiber material; and
the first conductive element is configured to form a plurality of interdigitated coupled elements of a capacitor, including:
　a first coupled element comprising a first set of fingers interwoven into the first fabric layer along the long axis of the first conductive element, the first set of fingers physically and electrically connected by and extending along a first direction from a first base embroidered into the first fabric layer, and
　a second coupled element, capacitively coupled to the first element, with a second set of fingers alternating with the first set of fingers and interwoven along the long axis of the first conductive element, the second set of fingers physically and electrically connected by and extending along a second direction from a second base embroidered into the first fabric layer, the second direction opposite and parallel to the first direction, the first set of fingers physically and electrically separated from the second set of fingers;
the measurement circuit is further configured to measure the first instrumented signal corresponding to a capacitance between the interdigitated coupled elements in response to the applied deformation; and
the deformation analyzer is further configured to compute the measure of stretch of the deformation sensing fabric, in the applied deformation, based on the measured capacitance.

12. A wearable device comprising:
one or more deformation sensing fabrics including:
　a fabric substrate comprising a first fabric layer that comprises a first electrically insulating fiber material, and
　a first conductive element woven into the first fabric layer, and configured to:
　　form a first strain gauge and a first instrumented signal is indicative of a change in resistance of the first strain gauge in response to a strain in the applied deformation applied to the fabric substrate along a length of the first strain gauge,
　　output the first instrumented signal, responsive to an applied stimulus signal;
a measurement circuit configured to measure the first instrumented signal from the first conductive element in response to an applied deformation;
a deformation analyzer configured to compute a measure of stretch of the deformation sensing fabric, in the applied deformation, based on the measured first instrumented signal from the first conductive element;
the fabric substrate further comprises a second fabric layer comprising a second electrically insulating fiber material and an electrically insulating interstitial layer formed between the first and second fabric layers;
the deformation sensing fabric further comprises a second conductive element interwoven into threads of the second fabric layer, the second conductive element configured to output a second instrumented signal in response to a strain in the applied deformation in the same first direction;
the second conductive element is configured to form a second strain gauge and the second instrumented signal is indicative of a change in resistance of the first strain gauge in response to a strain applied to the fabric substrate along a length of the first strain gauge;
the measurement circuit is further configured to measure the second instrumented signal from the second conductive element in response to the applied deformation, and a third instrumented signal between the first and second conductive elements indicative of a capacitance of the interstitial layer; and
the deformation analyzer is further configured to compute the measure of stretch and a measure of flex deformation of the deformation sensing fabric, in the applied deformation, based on the measured second and third instrumented signals.

13. A wearable device comprising:
one or more deformation sensing fabrics including:
　a fabric substrate comprising a first fabric layer that comprises a first electrically insulating fiber material, and
　a first conductive element woven into the first fabric layer, and configured to:
　　form a first strain gauge and a first instrumented signal is indicative of a change in resistance of the first strain gauge in response to a strain in the applied deformation applied to the fabric substrate along a length of the first strain gauge,
　　output the first instrumented signal, responsive to an applied stimulus signal;
a measurement circuit configured to measure the first instrumented signal from the first conductive element in response to an applied deformation;
a deformation analyzer configured to compute a measure of stretch of the deformation sensing fabric, in the applied deformation, based on the measured first instrumented signal from the first conductive element;
the fabric substrate further comprises a second fabric layer comprising a second electrically insulating fiber material and an electrically insulating interstitial layer formed between the first and second fabric layers;
the deformation sensing fabric further comprises a second conductive element interwoven into threads of the second fabric layer, the second conductive element configured to output a second instrumented signal in response to a strain in the applied deformation in second direction, the second direction perpendicular to the first direction, the second direction along a long-axis of the second conductive element;

the second conductive element is configured to form a second strain gauge and the second instrumented signal is indicative of a change in resistance of the second strain gauge in response to a strain applied to the fabric substrate along a length of the second strain gauge;

the measurement circuit is further configured to measure the second instrumented signal from the second conductive element in response to the applied deformation, and a third instrumented signal between the first and second conductive elements indicative of a capacitance of the interstitial layer; and the deformation analyzer is further configured to compute the measure of stretch and a measure of flex deformation of the deformation sensing fabric, in the applied deformation, based on the measured second and third instrumented signals.

14. A wearable device comprising:

one or more deformation sensing fabrics including:
- a fabric substrate comprising a first fabric layer, and
- a first conductive element woven into the first fabric layer, and configured to output a first instrumented signal, responsive to an applied stimulus signal, indicative of a measure of change in an electrical property of the first conductive element in response to a strain applied to the fabric substrate along a long-axis of the first conductive element;
- a measurement circuit configured to measure the first instrumented signal from the first conductive element in response to an applied deformation; and
- a deformation analyzer configured to compute a measure of stretch of the deformation sensing fabric, in the applied deformation, based on the measured first instrumented signal from the first conductive element the first fabric layer comprises an electrically insulating fiber material; and the first conductive element is configured to form a plurality of interdigitated electrodes of a capacitor, including:
- a first coupled element comprising a first set of fingers interwoven into the first fabric layer along the long axis of the first conductive element, the first set of fingers physically and electrically connected by and extending along a first direction from a first base embroidered into the first fabric layer, and
- a second coupled element, capacitively coupled with the first coupled element, with a second set of fingers alternating with the first set of fingers and interwoven along the long axis of the first conductive element, the second set of fingers physically and electrically connected by and extending along a second direction from a second base embroidered into the first fabric layer, the second direction opposite and parallel to the first direction, the first set of fingers physically and electrically separated from the second set of fingers.

* * * * *

UNITED STATES PATENT AND TRADEMARK OFFICE
CERTIFICATE OF CORRECTION

PATENT NO. : 9,816,799 B2
APPLICATION NO. : 14/975465
DATED : November 14, 2017
INVENTOR(S) : Sean Jason Keller et al.

It is certified that error appears in the above-identified patent and that said Letters Patent is hereby corrected as shown below:

Column 20, Line 59, in Claim 10 after "applied deformation in," insert -- the --.

Signed and Sealed this
Twenty-fourth Day of April, 2018

Andrei Iancu
*Director of the United States Patent and Trademark Office*